(12) United States Patent
Nemoto et al.

(10) Patent No.: US 8,211,057 B2
(45) Date of Patent: Jul. 3, 2012

(54) CHEMICAL LIQUID INJECTION SYSTEM

(75) Inventors: Shigeru Nemoto, Tokyo (JP); Masahiro Sakakibara, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 324 days.

(21) Appl. No.: 12/066,490

(22) PCT Filed: Sep. 12, 2006

(86) PCT No.: PCT/JP2006/318058
§ 371 (c)(1),
(2), (4) Date: Mar. 11, 2008

(87) PCT Pub. No.: WO2007/032341
PCT Pub. Date: Mar. 22, 2007

(65) Prior Publication Data
US 2009/0156931 A1    Jun. 18, 2009

(30) Foreign Application Priority Data
Sep. 12, 2005    (JP) .................................. 2005-263308

(51) Int. Cl.
*A61M 1/00* (2006.01)
*A61B 6/00* (2006.01)
(52) U.S. Cl. ..................... 604/121; 600/432; 340/572.7; 343/866
(58) Field of Classification Search ............... 604/65–69, 604/111, 131, 151–153, 189; 340/572.7; 373/866–877; 343/866–877
See application file for complete search history.

(56) References Cited

U.S. PATENT DOCUMENTS

| | | | |
|---|---|---|---|
| 5,912,622 A * | 6/1999 | Endo et al. ................. 340/572.5 |
| 7,686,789 B2 * | 3/2010 | Nemoto et al. ............... 604/246 |
| 2004/0073177 A1 | 4/2004 | Hickle | |
| 2005/0110640 A1 * | 5/2005 | Chung ........................ 340/572.1 |
| 2006/0208899 A1 * | 9/2006 | Suzuki et al. ............... 340/572.7 |
| 2007/0167919 A1 * | 7/2007 | Nemoto et al. ............... 604/189 |
| 2009/0018494 A1 * | 1/2009 | Nemoto et al. ................. 604/67 |
| 2009/0131756 A1 * | 5/2009 | Nemoto ........................ 600/300 |

FOREIGN PATENT DOCUMENTS
DE        197 33 849 A1    4/1998
(Continued)

OTHER PUBLICATIONS
Apr. 30, 2010 First Office Action for Chinese Application No. 200680041637.9.
(Continued)

*Primary Examiner* — Quynh-Nhu H Vu
(74) *Attorney, Agent, or Firm* — Knobbe, Martens, Olson & Bear, LLP

(57) ABSTRACT

A chemical liquid injector comprises liquid syringe 200 and a chemical liquid injector. Liquid syringe 200 has cylinder member 210, a piston member and RFID tag 230 put on an outer circumference of cylinder member 210. The chemical liquid injector has cylinder holding mechanism 120 for holding cylinder member 210, a piston driving mechanism for driving the piston member and an RFID reader. The RFID reader has reader antennas 132L, 132R placed opposite to a tag antenna so as to be able to receive data from RFID tag 230 with cylinder member 210 is appropriately held by the cylinder holding mechanism. The piston driving mechanism is permitted to operate only when the RFID reader receives data from RFID tag 230.

21 Claims, 16 Drawing Sheets

FOREIGN PATENT DOCUMENTS

| | | |
|---|---|---|
| EP | 1 433 456 A1 | 6/2004 |
| JP | 10-162260 | 6/1998 |
| JP | 2005-525885 | 9/2005 |
| WO | WO 03/024385 A1 | 3/2003 |
| WO | WO 03/097156 A1 | 11/2003 |

OTHER PUBLICATIONS

Office Action mailed Oct. 26, 2011 in Japanese Application No. 2007-535479.

* cited by examiner

CHEMICAL LIQUID INJECTION SYSTEM

CROSS REFERENCE TO RELATED APPLICATION

This application claims the benefit and priority to and is a U.S. National Phase of PCT International Application Number PCT/JP2006/318058, filed on Sep. 12, 2006, designating the United States of America, which claims priority under 35 U.S.C. §119 to Japanese Application Number 2005-263308 filed on Sep. 12, 2005. The disclosures of the above-described applications are hereby incorporated by reference in their entirety.

TECHNICAL FIELD

The present invention relates to a chemical liquid injection system for injecting a liquid into a patient from a liquid syringe with a chemical liquid injector, and more particularly, to a chemical liquid injection system for injecting a contrast medium into a patient whose diagnostic images are taken by an imaging diagnostic apparatus such as a CT (Computed Tomography) scanner.

BACKGROUND ART

Presently available imaging diagnostic apparatuses for capturing diagnostic images of patients include CT scanners, MRI (Magnetic Resonance Imaging) apparatuses, PET (Positron Emission Tomography) apparatuses, ultrasonic diagnostic apparatuses, CT angiography apparatuses, MRA (MR angiography) apparatuses and the like. When the above-mentioned imaging diagnostic apparatuses are used, a liquid such as a contrast medium and physiological saline may be injected into a patient. Chemical liquid injectors for automatically performing the injection have been put into practical use.

Such a chemical liquid injector has a piston driving mechanism formed of a driving motor, a slider mechanism and the like, for example. A liquid syringe is removably mounted on the chemical liquid injector. The liquid syringe typically comprises a cylinder member and a piston member slidably inserted in the cylinder member.

More particularly, the cylinder member is formed in a cylindrical shape having a closed leading end and an opened trailing end. The cylinder member has a conduit formed at the center of the leading end and an annular cylinder flange formed on the outer circumference of the trailing end. The piston member is slidably inserted into the interior of cylinder member from the trailing end.

There are a pre-filled type and a type filled with nothing in the liquid syringe. The liquid syringe of the pre-filled type includes a cylinder member filled with a liquid and is wholly sealed by a packing material for shipment. In the liquid syringe of the type filled with nothing, a cylinder member is filled with a desired liquid by a user. For simplicity, the following description will be made assuming that the liquid syringe of the pre-filled type is used.

For injecting the liquid into a patient from the liquid syringe of the abovementioned type, an operator prepares for a liquid syringe containing an appropriate liquid and takes out the liquid syringe from the packing material. The operator connects the liquid syringe to the patient through an extension tube and mounts the liquid syringe on the chemical liquid injector. The mounting on the chemical liquid injector is performed by causing a flange holding mechanism of the chemical liquid injector to hold the cylinder flange. In this state, the chemical liquid injector operates the piston driving mechanism in response to a predetermined operation by the operator. This presses the piston member into the cylinder member to inject the liquid into the patient from the liquid syringe.

The operator determines the rate at which the liquid is injected and the total quantity of the liquid to be injected in view of the type of the liquid and the like, and enters data representing the rate and total quantity into the chemical liquid injector. The chemical liquid injector injects the liquid into the patient based on the entered data. For example, if a contrast medium is injected as the liquid, the image contrast of the patient is changed to allow the imaging diagnostic apparatus to capture a favorable diagnostic image of the patient.

Some chemical liquid injectors can inject physiological saline as well as the contrast medium into the patient. In such a chemical liquid injector, the operator enters as desired an instruction to inject the physiological saline following the completion of the injection of the contrast medium, together with data representing the injection rate and total quantity of the physiological saline, into the chemical liquid injector. The chemical liquid injector first injects the contrast medium into the patient based on the entered data and then automatically injects the physiological saline. Consequently, the subsequently injected physiological saline can push the contrast medium to reduce the consumption of the contrast medium and also can reduce artifacts in the captured image.

The contrast medium has a high viscosity. Since the chemical liquid injector can press the piston member into the cylinder member at high pressure, the injector is preferably used for injection of the contrast medium. To insert the piston member into the cylinder member at high pressure, however, the cylinder member needs to be held securely.

Thus, a chemical liquid injector invented and conducted by the applicant of the present application includes a pair of metallic flange holding members supported openably or closably. The paired flange holding members hold individually the left and the right of a cylinder flange of a liquid syringe put on a chemical liquid injector (see, for example, Japanese Patent Laid-Open No. 2004-187849).

In the chemical liquid injector as described above, the pair of metallic flange holding members can securely hold the cylinder flange of the liquid syringe. In consequence, the piston member can be inserted into the cylinder member at high pressure to satisfactorily inject the contrast medium with high viscosity and the like into a patient.

In typical liquid syringes currently used, the cylinder flange has a pair of flat portions in parallel at opposite positions on the circular outer circumference in order to prevent unnecessary rolling and the like of the liquid syringe. The conventional chemical liquid injector is formed to hold the circular portion of the cylinder flange with the flange holding members, and the operator needs to ensure the holding of the circular portion of the cylinder flange with the flange holding members without fail.

If the flange holding members hold the flat portions of the cylinder flange, however, the operator may see it as if the liquid syringe was appropriately held in the chemical liquid injector. In this case, since a smaller area of the cylinder flange is held by the flange holding members, the cylinder flange may be broken easily.

In addition, for injecting the liquid from the liquid syringe into the patient in the abovementioned chemical liquid injector, the operator needs to select the appropriate liquid syringe in order to inject the appropriate liquid. However, since some liquid syringes have the same or similar appearances even when they contain different types of liquid, this leads to the possibility that the operator may mount the liquid syringe containing an inappropriate liquid on the chemical liquid injector.

In some cases, an improper product for a chemical liquid injector may be used as a liquid syringe. In this case, the inappropriate performance thereof such as low resistance to pressure may cause medical malpractice. The liquid syringe of the pre-filled type should be discarded after it is used once in order to prevent infection and the like. As for the currently available chemical liquid injectors, however, it is impossible to prevent reuse of a liquid syringe reliably after it is used once.

As described above, the operator needs to enter data representing the injection rate and total quantity of the liquid and the like for each of the liquid and the liquid syringe into the chemical liquid injector. Since the entry operation is complicated and difficult for an unskilled operator, entry of incorrect numerical values cannot be avoided. The currently available contrast media contain active ingredients which differ in concentration severalfold at maximum. If correct numerical values are not entered, the patient may be injected with the contrast medium of the quantity which is several times larger than or a fraction of the appropriate quantity.

The operator needs to enter data representing the injection rate or the like of the liquid into the chemical liquid injector in some cases based on the area to be imaged and the weight of the patient. The entry operation is also complicated and erroneous entry cannot be prevented. The present applicant has applied that a contrast medium is injected at a variable rate to improve the resulting image contrast (Japanese Patent Laid-Open No. 2004-113475). However, it is not easy to enter the data representing such a variable pattern into the chemical liquid injector.

DISCLOSURE OF THE INVENTION

The present invention has been made in view of the above-mentioned problems, and it is an object thereof to provide a chemical liquid injection system which can automatically prevent driving of a piston driving mechanism while a liquid syringe is not appropriately held by a cylinder holding mechanism.

The chemical liquid injection system according to the present invention includes a liquid syringe and a chemical liquid injector. The liquid syringe includes a cylinder member, a piston member, and an RFID tag. The chemical liquid injector includes a cylinder holding mechanism, a piston driving mechanism, an RFID reader, operation control means, and an antenna placement portion.

The piston member of the liquid syringe is slidably inserted into the cylinder member. The RFID tag is put on the outer circumference of the cylinder member and includes a tag antenna formed of a loop antenna.

The cylinder holding mechanism holds the cylinder member. The piston driving mechanism presses the piston member into the held cylinder member. The RFID reader receives data from the RFID tag through electromagnetic induction via a reader antenna formed of a loop antenna. The operation control means permits operation of the piston driving mechanism only when the data is received. The antenna placement portion places the reader antenna at a position opposite to the tag antenna generally in parallel while the cylinder member is appropriately held by the cylinder holding mechanism.

Thus, in the chemical liquid injection system of the present invention, since the reader antenna formed of the loop antenna faces the tag antenna generally in parallel while the cylinder member is appropriately held by the cylinder holding mechanism, the RFID reader and the RFID tag can communicate with each other and the operation control means permits the operation of the piston driving mechanism. However, if the cylinder member is not appropriately held by the cylinder holding mechanism, the reader antenna does not face the tag antenna generally in parallel, which disables communication between the RFID reader and the RFID tag, and the operation control means does not permit the operation of the piston driving mechanism.

Various means referred to in the present invention may be arranged to perform their functions, and may comprise dedicated hardware for performing a predetermined function, a data processing apparatus whose predetermined function is given by a computer program, a predetermined function performed in a data processing apparatus according to a computer program, or a combination thereof.

Various components referred to in the present invention do not need to be a separate entity. A plurality of components may be constructed as one member, a single component may be formed of a plurality of members, a certain component may be part of another component, or a certain component may have a portion overlapping a portion of another component. Although the forward, rearward, leftward, rightward, upward, and downward directions are specified in the present invention, these directions are defined for convenience to simply describe the relative relationship between components of the present invention and the definition does not limit any direction in manufacture or actual use when the present invention is implemented.

In the chemical liquid injection system, only when the liquid syringe is appropriately held by the cylinder holding mechanism, the data on the RFID tag can be received by the RFID reader. Then, the piston driving mechanism can press the piston member into the cylinder member. The pressing of the piston member into the cylinder member can be automatically prevented while the liquid syringe is not appropriately held.

DESCRIPTION OF REFERENCE NUMERALS

100 CHEMICAL LIQUID INJECTOR
113 HEAD BODY
114 CONCAVE PORTION
116 PISTON DRIVING MECHANISM
120 CYLINDER HOLDING MECHANISM
130 RFID READER
131 READER CIRCUIT
132, 160 READER ANTENNA
135 INSULATING SUBSTRATE
200 LIQUID SYRINGE
210 CYLINDER MEMBER
220 PISTON MEMBER
230 RFID TAG
232 RFID CHIP
233, 241, 251 TAG ANTENNA
300 CT SCANNER
1000 CHEMICAL LIQUID INJECTION SYSTEM

BEST MODE FOR CARRYING OUT THE INVENTION

An embodiment of the present invention will hereinafter be described with reference to the figures. Chemical liquid injection system 1000 of the embodiment according to the present invention comprises chemical liquid injector 100, liquid syringe 200, and CT scanner 300 which serves an imaging diagnostic apparatus. The system is provided for taking diagnostic images of a patient (not shown) injected with a liquid such as a contrast medium, described later in detail.

Figure 4:
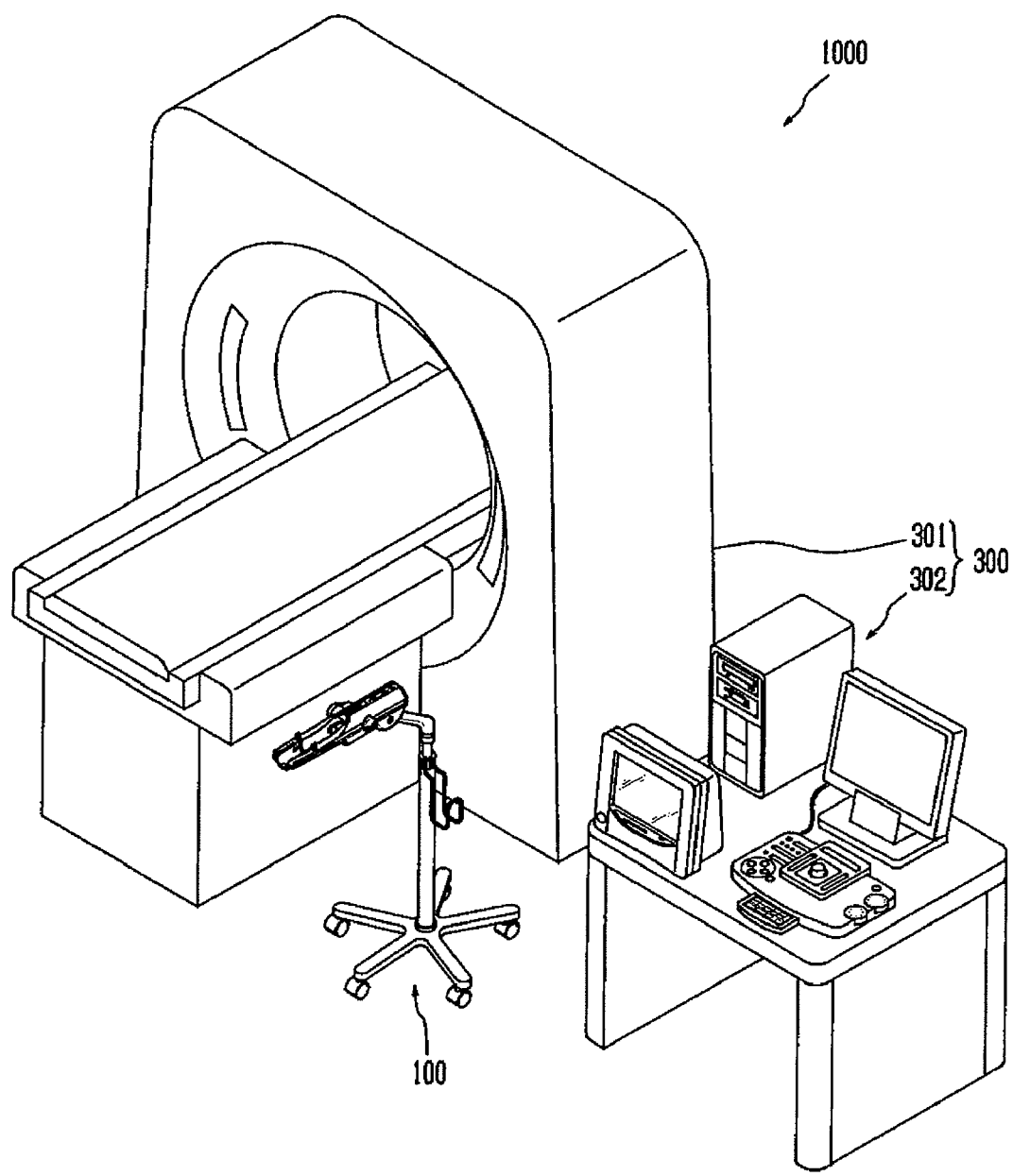
FIG. 4 is a perspective view showing the outer appearance of a CT scanner serving as an imaging diagnostic apparatus.
Figure 5:
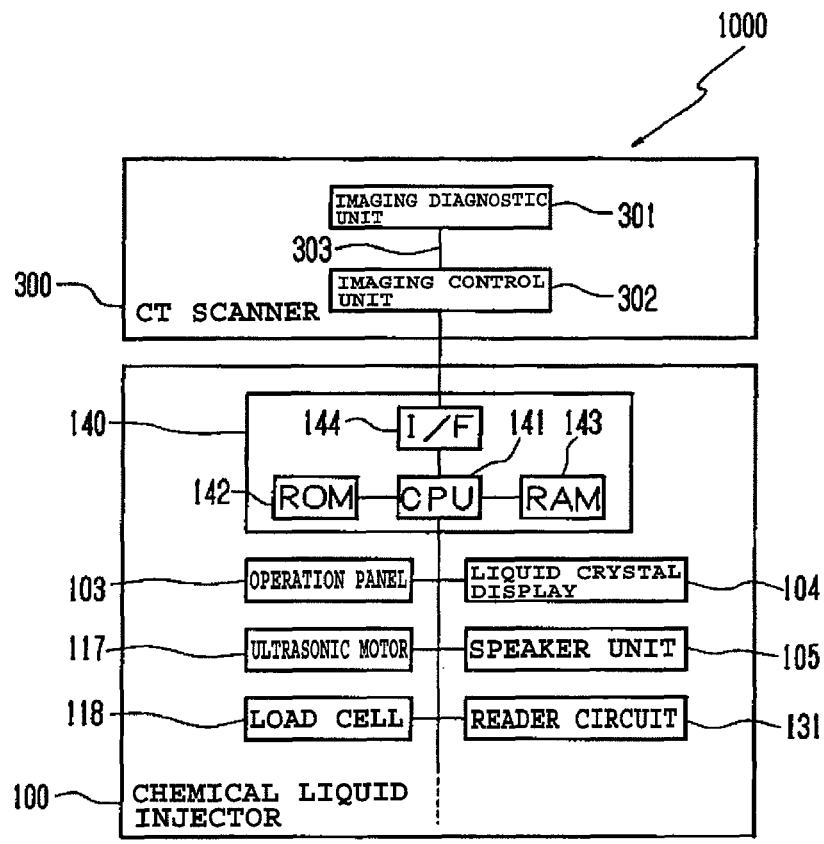
FIG. 5 is a block diagram showing the circuit structure of a chemical liquid injection system.

As shown in FIGS. 4 and 5, CT scanner 300 includes imaging diagnostic unit 301 and imaging control unit 302. Imaging diagnostic unit 301 and imaging control unit 302 are wire-connected through communication network 303. Imaging diagnostic unit 301 shoots diagnostic images of a patient. Imaging control unit 302 controls the operation of imaging diagnostic unit 301.

Figure 2:
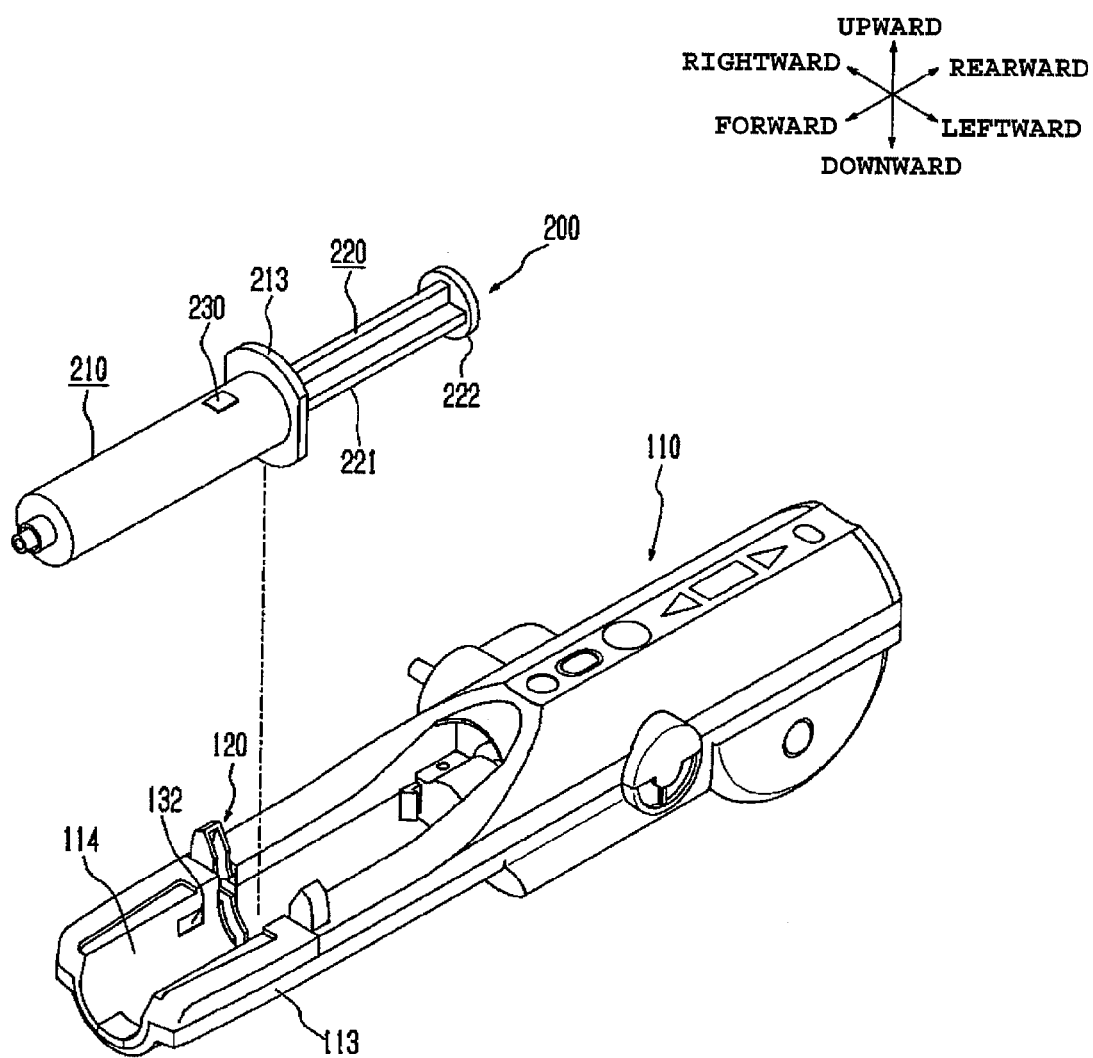
FIG. 2 is a perspective view showing the liquid syringe mounted on an injection head of the chemical liquid injector.
Figure 6:
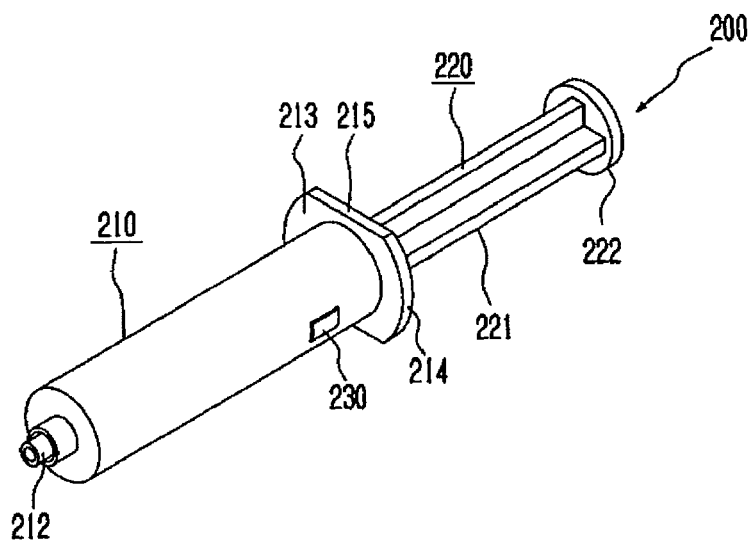
FIG. 6 is a perspective view showing the outer appearance of the liquid syringe.

As shown in FIGS. 2 and 6, liquid syringe 200 comprises cylinder member 210 and piston member 220. Piston member 220 is slidably inserted into cylinder member 210. Cylinder member 210 includes tubular cylinder body 211. Cylinder body 211 has conduit 212 formed at its closed leading end.

The trailing end of cylinder body 211 is opened, and piston member 220 is inserted from the opening into the interior of cylinder body 211. Cylinder member 210 has cylinder flange 213 formed in an annular shape on the outer circumference of the trailing end of cylinder body 211. Piston member 220 has piston flange 222 formed in an annular shape on the outer circumference of the trailing end of piston body 221. Cylinder member 210 is made of resin which is a nonmagnetic material and, for example, has a thickness of approximately 1.5 mm to 2.0 mm.

In chemical liquid injection system 1000 of the embodiment, at least some of liquid syringes 200 to be used are of the pre-filled type. Liquid syringe 200 of the pre-filled type is shipped with cylinder member 210 filled with a liquid. RFID (Radio Frequency Identification) tag 230 is placed on cylinder member 210 of liquid syringe 200. RFID tag 230 has various types of data about liquid syringe 200 recorded thereon such as the name, the identification data indicating the pre-filled type or the type filled with nothing, the identification data for each item, the capacity, the resistance to pressure of cylinder member 210, the inner diameter of cylinder member 210, and the stroke of piston member 220.

When liquid syringe 200 of the pre-filled type is used, RFID tag 230 also has various types of data about the contained liquid recorded thereon such as the name, the ingredients, the viscosity, the expiration date, and the identification data indicating whether the liquid is for CT or MR. When a contrast medium is contained as the liquid contained in liquid syringe 200 of the pre-filled type, RFID tag 230 also has data recorded thereon, as required, such as the variable pattern with which the injection rate is changed over time.

Figure 7:
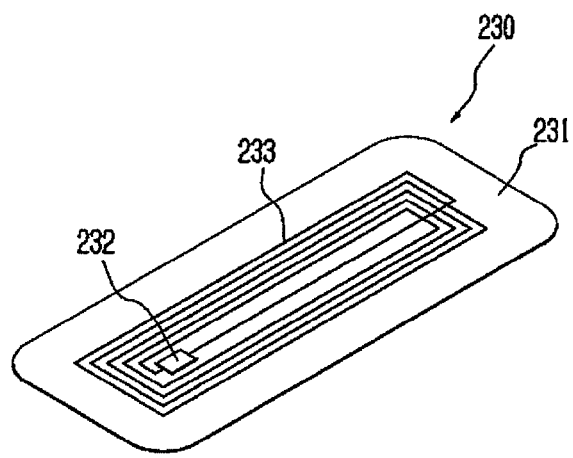
FIG. 7 is a perspective view showing the outer appearance of an RFID tag.

As shown in FIG. 7, RFID tag 230 has chip body 231 formed of resin sheet in an elongated shape. RFID chip 232 is enclosed close to one end of chip body 231. Tag antenna 233 formed of flat loop antenna is also provided in an elongated shape with printed wiring on chip body 231. Tag antenna 233 is connected to RFID chip 232.

Chip body 231 is white in color on its front side, for example. Thus, various types of information can be provided on the front side through printing or the like. Chip body 231 has an adhesive material (not shown) applied to the back side thereof. RFID tag 230 is put on the outer circumference of cylinder member 210 by the adhesive material.

As shown in FIGS. 1 and 6, cylinder flange 213 has a pair of flat portions 215 in parallel at opposite positions on its circular outer circumference 214. RFID tag 230 is disposed such that it is located on the left or right of cylinder member 210 when the paired flat portions 215 are located at the top and bottom. RFID tag 230 is formed in the elongated shape as described above, and the longitudinal direction of tag antenna 233 corresponds to the longitudinal direction of cylinder member 210.

Figure 3:
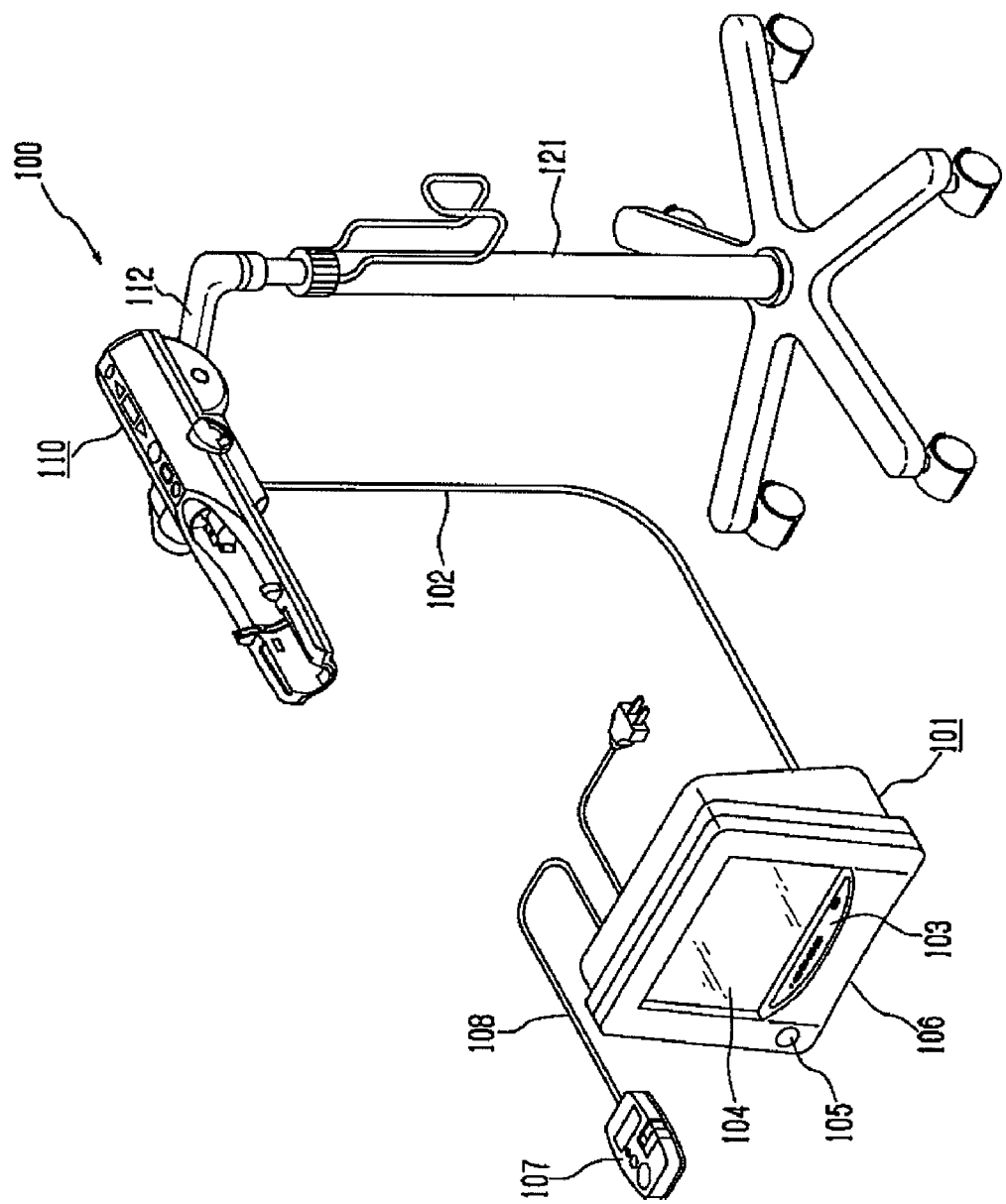
FIG. 3 is a perspective view showing the outer appearance of the chemical liquid injector.

As shown in FIG. 3, chemical liquid injector 100 of the embodiment has injection control unit 101 and injection head 110 constructed as separate components. Injection control unit 101 and injection head 110 are wire-connected through communication cable 102. Injection head 110 drives chemical liquid syringe 200 mounted thereon to inject a liquid therefrom into a patient. Injection control unit 101 controls the operation of injection head 110.

Injection head 110 is attached to the upper end of caster stand 111 by movable arm 112. As shown in FIG. 2, head body 113 serving as a cylinder holding member of injection head 110 has concave portion 114 formed as a semi-cylindrical groove in the upper surface for removably mounting cylinder member 210 of chemical liquid syringe 200.

Cylinder holding mechanism 120 is formed in the forward section of concave portion 114 for removably holding cylinder flange 211 of liquid syringe 200. Piston driving mechanism 116 is placed in the rearward section of concave portion 114 for holding and sliding piston flange 222.

As shown in FIG. 5, piston driving mechanism 116 has ultrasonic motor 117 as a driving source which is free from generation of magnetic field even in operation, and slides piston member 220 through a screw mechanism (not shown) or the like. Load cell 118 is also contained in piston driving mechanism 116. Load cell 118 detects the pressure applied to piston member 220.

Figure 1A:
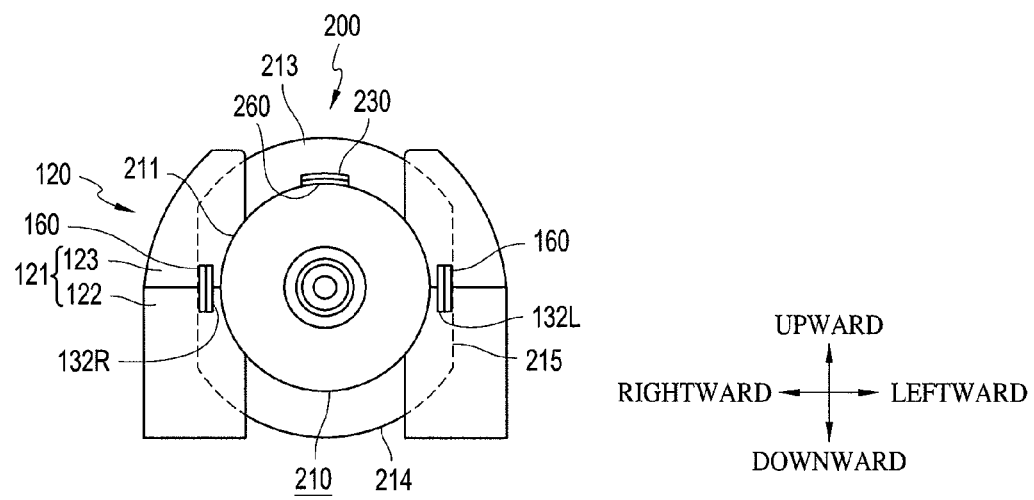
FIG. 1A is a front view schematically showing a liquid syringe inappropriately put in a chemical liquid injector according to an embodiment of the present invention.
Figure 1B:
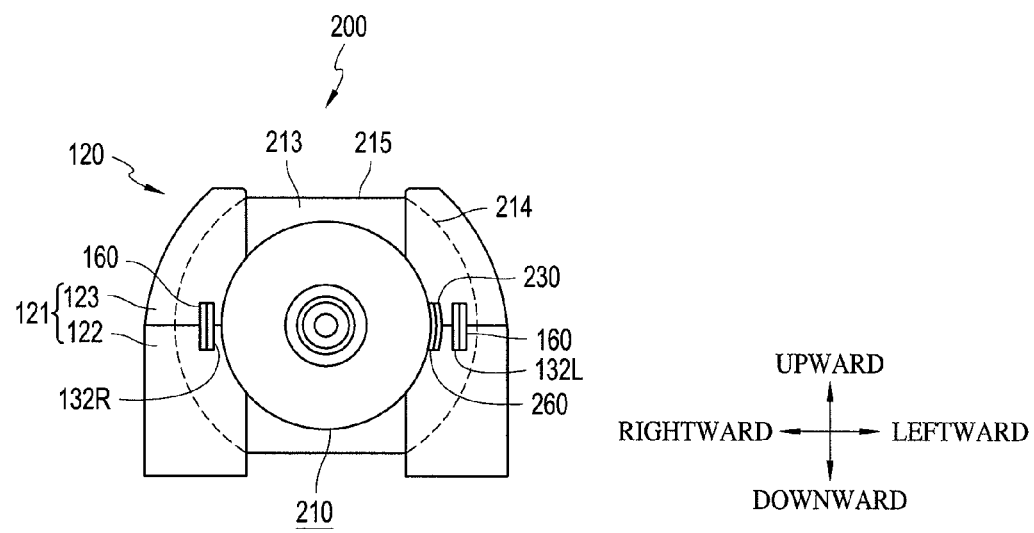
FIG. 1B is a front view schematically showing the liquid syringe appropriately put in the chemical liquid injector according to the embodiment of the present invention.

As shown in FIGS. 1A and 1B, cylinder holding mechanism 120 has a pair of flange holding members 121 on the left and right. The paired left and right flange holding members 121 hold individually the left and right of cylinder flange 213 of liquid syringe 200 put from above. More particularly, flange holding members 121 include fixed holding members 122 and movable holding members 123, both of which are made of high-strength metal such as stainless alloy.

Each of fixed holding mechanisms 122 is fixed to the bottom of concave portion 114 of injection head 110. Movable holding members 123 are pivoted openably or closably leftward and rightward at the positions where they are bonded to associated fixed holding members 122 from above. Fixed holding member 122 and movable holding member 123 have an arc-shaped concave groove in the inner surfaces (see FIG. 2). Cylinder flange 213 of liquid syringe 200 is fitted into the groove.

Chemical liquid injector 100 of the embodiment includes RFID reader 130. RFID reader 130 wirelessly communicates with RFID tag 230 on liquid syringe 200 through electromagnetic induction. RFID reader 130 has reader circuit 131 and reader antenna 132. Reader circuit 131 is mounted on injection control unit 101.

Figure 9:
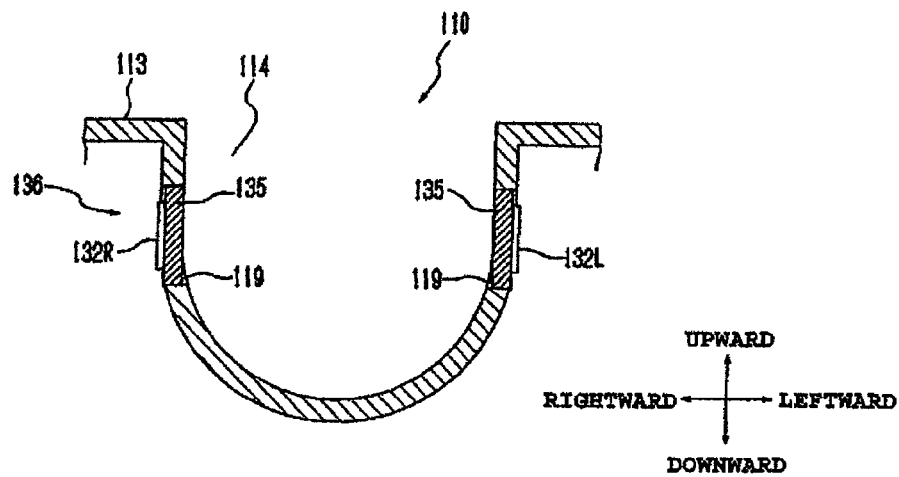
FIG. 9 is a longitudinal section showing the assembly structure of the main portions of the injection head.
Figure 10A:
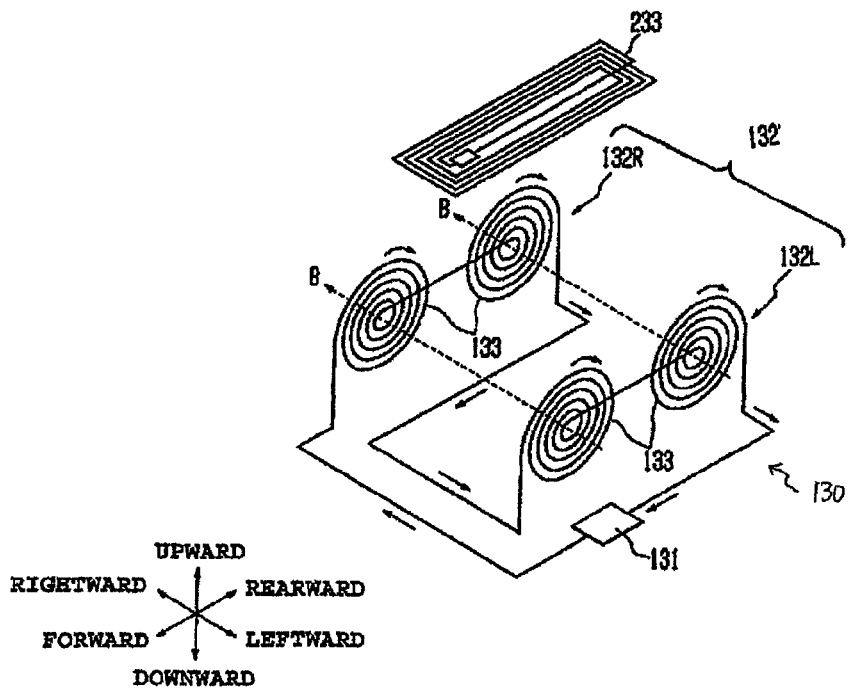
FIG. 10A is a schematic diagram showing the principles of electromagnetic induction between a tag antenna and a reader antenna.
Figure 10B:
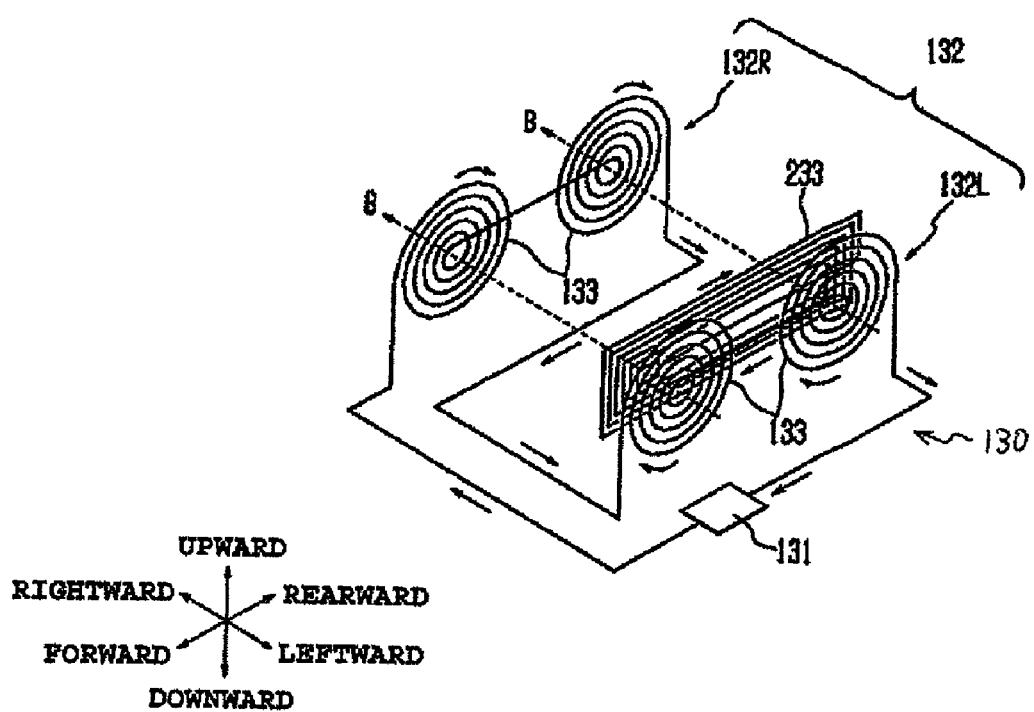
FIG. 10B is a schematic diagram showing the principles of electromagnetic induction between the tag antenna and the reader antenna.

As shown in FIGS. 10A and 10B, reader antenna 132 is formed of a single wire as a pair of reader antennas 132L and 132R on the left and right. As shown in FIGS. 1 and 9, reader antennas 132L and 132R are placed individually on the left and right of concave portion 114 of injection head 110.

Figure 8:
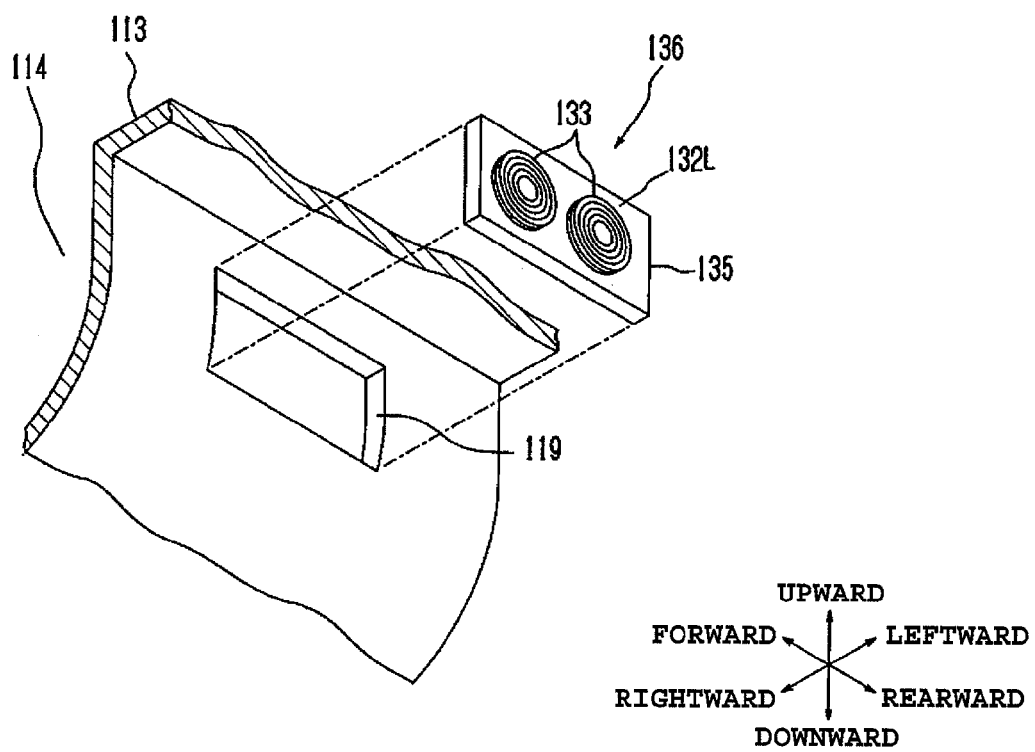
FIG. 8 is an exploded perspective view showing the assembly structure of main portions of the injection head.

As shown in FIGS. 8, 10A and 10B, each of reader antennas 132L and 132R has two loop antennas 133. These loop antennas 133 are placed in the front and the back. Each of loop antennas 133 of reader antennas 132L and 132R is wound with the axis placed in the left-right direction and is formed in a flat shape in parallel with the forward, rearward, upward, and downward directions.

As shown in FIGS. 10A and 10B, each of loop antennas 133 of reader antennas 132L and 132R is wound clockwise when viewed from the left, for example. Forward loop antenna 133 on the left is connected to rearward loop antenna 133 on the right, while rearward loop antenna 133 on the left is connected to forward loop antenna 133 on the right.

Consequently, when an electric current is passed through reader antenna 132 formed of the single wire as described above, the current flows in the same direction in all of the four loop antennas 133 to produce central magnetic fields B in the same direction from loop antennas 133. Since reader antennas 132L and 132R are arranged on the left and right, the positions of central magnetic fields B of loop antennas 133 located on the left and right coincide.

As shown in FIGS. 8 and 9, reader antennas 132L and 132R as described above are individually mounted on the front side of rectangular insulating substrates 135 serving as an antenna placement mechanism, thereby forming a pair of antenna units 136 on the left and right. Head body 113 is made of metal such as an alloy of aluminum and has rectangular through holes 119 elongated in the front-back direction in both sides of concave portion 114 on the left and right.

Insulating substrates 135 are fitted into through holes 119 to place reader antennas 132L and 132R individually on both sides of concave portion 114 on the left and right. Such placement causes reader antennas 132L and 132R on the left and right to be disposed at opposite positions on the left and right across the axis of cylinder member 210 put in concave portion 114 as shown in FIG. 1. The longitudinal directions of reader antennas 132L and 132R coincide with the longitudinal direction of cylinder member 210 put in concave portion 114 as shown in FIGS. 2 and 8.

Each of through holes 119 and insulating substrates 135 is formed, for example, in a rectangular shape of 30 mm×70 mm, and each of loop antennas 133 of reader antenna 132 is formed in a circular shape having the maximum diameter of 20 mm. Each of loop antennas 133 of reader antenna 132 has an outer edge 3.0 mm away from the outer edge of insulating substrate 135 at minimum, for example, so that a spatial distance of 3.0 mm or more is provided between the outer edge of reader antenna 132 and the inner edge of through hole 119 of head body 113.

RFID tag 230 and RFID reader 130 of the embodiment wirelessly communicate with each other, for example at a frequency of 13.56 MHz. Thus, RFID reader 130 has inductance, capacitance and the like at its portions adjusted to provide a resonance point of 13.56 MHz of reader antenna 132. An example of RFID tag 230 for wireless communication at a frequency of 13.56 MHz is an MM tag (product name) having a size of 18 mm×50 mm.

As shown in FIG. 5, injection control unit 101 connected to injection head 110 through communication cable 102 and formed as described above contains a computer unit 140 and is wire-connected to imaging control unit 302 of CT scanner 300 through communication network 304.

As shown in FIG. 3, injection control unit 101 has operation panel 103, liquid crystal display 104 serving as a data display means, and speaker unit 105, all of which are disposed on the front face of unit housing 106. Injection control unit 101 is wire-connected to controller unit 107 as a separate component through connector 108.

Reader circuit 131 of RFID reader 130 is also mounted on injection control unit 101. Reader circuit 131 on injection control unit 101 is connected to reader antenna 132 on injection head 110 through a dedicated coaxial cable (not shown).

As shown in FIG. 5, in chemical liquid injector 100 of the embodiment, the abovementioned various devices such as reader circuit 131 are connected to computer unit 140. Computer unit 140 integrates and controls those various devices. Computer unit 140 is formed of a so-called one-chip microcomputer provided with hardware such as CPU (Central Processing Unit) 141, ROM (Read Only Memory) 142, RAM (Random Access Memory) 143, I/F (Interface) 144 and the like. Computer unit 140 has an appropriate computer program installed as firmware or the like on an information storage medium such as ROM 142, and CPU 141 executes various types of processing in accordance with the computer program.

Figure 11:
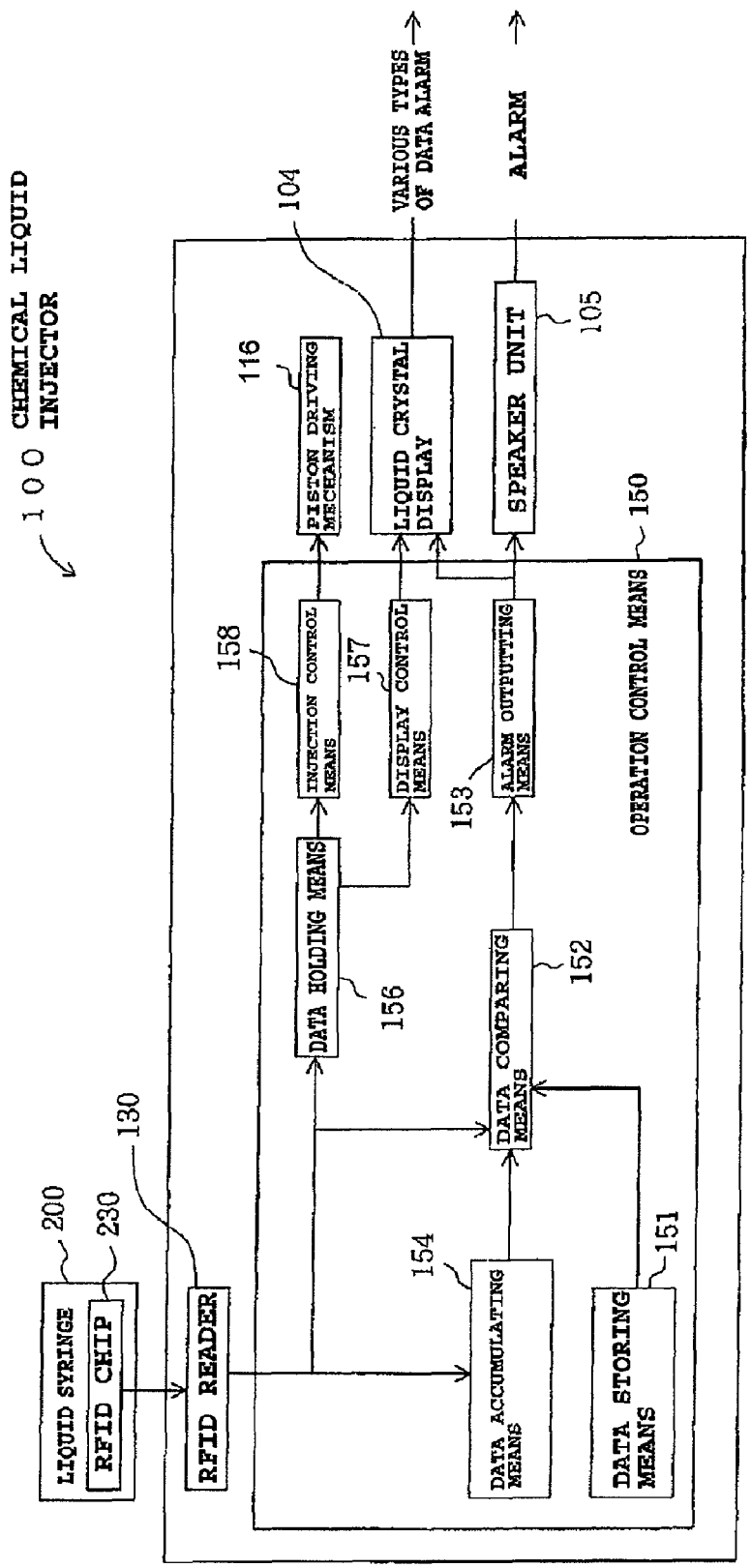
FIG. 11 is a schematic block diagram showing the logical structure of the chemical liquid injector.

In chemical liquid injector 100 of the embodiment, computer unit 140 operates in accordance with the computer program installed as described above to logically have operation control means 150 as shown in FIG. 11. Operation control means 150 logically includes various means such as data storing means 151, data comparing means 152, alarm outputting means 153, data accumulating means 154, data holding means 156, display control means 157, and injection control means 158.

Operation control means 150 corresponds to the function of CPU 141 which performs predetermined operations in accordance with the computer program installed in ROM 142 or the like and the recorded data wirelessly received from RFID tag 230.

Data storing means 151 corresponds to the store area of RAM 143 and the like recognized by CPU 141 and stores data about predetermined check conditions. Data comparing means 152 compares the stored data about check conditions with the recorded data wirelessly received from RFID tag 230. Alarm outputting means 153 outputs an alarm in accordance with the comparison result.

More particularly, RAM 143 has data for identifying usable liquid syringes 200 registered thereon in the check conditions. When RFID reader 130 receives the recorded data from RFID tag 230 on liquid syringe 200, the received identification data of liquid syringe 200 is compared with the identification data registered in RAM 143.

When the received identification data is not match registered, a guidance message, for example "This product not registered as usable syringe. Check if it is usable" is output as an alarm with display on liquid crystal display 104 and with sound from speaker unit 105.

The current date and time is constantly updated and held in the check conditions in RAM 143. When the expiration date is received from RFID tag 230 on liquid syringe 200, the expiration date is compared with the current date and time. If the current data and time is after the expiration date, a guidance message, for example "Expiration date of this product elapsed. Use new one" is output as an alarm with display on liquid crystal display 104 and with sound from speaker unit 105.

In the pre-filled type, the production number of each liquid syringe 200 is also set on RFID tag 230. Thus, data accumulating means 154 stores the data of the production number of liquid syringe 200 of the pre-filled type put on injection head 110 and used to perform injection operation.

In this case, data comparing means 152 compares the stored production numbers with the production number received from RFID tag 230. When a match is found between the compared production numbers, alarm outputting means 153 outputs a guidance message, for example "This pre-filled syringe used previously. Use new one" as an alarm with display on liquid crystal display 104 and with sound from speaker unit 105.

Data holding means 156 holds the recorded data received from RFID tag 230. Display control means 157 displays the held recorded data on liquid crystal display 104. Injection control means 158 controls the operation of piston driving mechanism 116 based on the held recorded data.

More specifically, RFID tag 230 has various types of data recorded thereon such as the name, the resistance to pressure, and the capacity of liquid syringe 200 as well as the name, the ingredients, and the expiration date of the liquid contained in liquid syringe 200. The recorded data is temporarily held in RAM 143 and presented on liquid crystal display 104.

When the control data for piston driving mechanism 116 is recorded on RFID tag 230, the control data is held in RAM 143. CPU 141 controls the operation of piston driving mechanism 116 based on the held control data. For example, when a variable pattern for changing the injection rate of the contrast medium over time is recorded as data on RFID tag 230, CPU 141 changes the operation rate of piston driving mechanism 116 over time in accordance with the variable pattern.

When the resistance to pressure is recorded as data on RFID tag 230, CPU 141 controls the operation of piston driving mechanism 116 such that the resistance to pressure held as data in RAM 143 is not exceeded on the basis of the pressure detected by load cell 118. When the capacity of liquid syringe 200 is recorded as data on RFID tag 230, CPU 141 controls the operation of piston driving mechanism 116 based on the capacity held as data in RAM 143.

The abovementioned various means of chemical liquid injector 100 are accomplished by pieces of hardware including liquid crystal display 104 as required, and they are mainly implemented by CPU 141 as a piece of hardware functioning in accordance with the resources and the computer program stored on an information storage medium such as ROM 142.

Such a computer program is stored in an information storage medium such as RAM 143 as software for causing CPU 141 or the like to perform processing operations including the comparison of the check conditions stored as data in RAM 143 and the like with the recorded data received from RFID tag 230 when RFID reader 130 receives the recorded data from RFID tag 230, the output of the alarm with display on liquid crystal display 104 or the like in accordance with the comparison result, the storing of the production number of liquid syringe 200 mounted and used to perform injection operation in RAM 143 or the like, the comparison of the stored production numbers with the production number received from RFID tag 230, the output of the alarm with display or the like on liquid crystal display 104 in accordance with the comparison result, the holding of the recorded data received from RFID tag 230 in RAM 143 or the like, the display of the held recorded data on liquid crystal display 104, and the control of the operation of piston driving mechanism 116 in accordance with the held recorded data.

Operation of the Embodiment

When chemical liquid injection system 1000 of the embodiment is used in the abovementioned structure, injection head 110 of chemical liquid injector 100 is placed near imaging unit 301 of CT scanner 300, and liquid syringe 200 or the like is prepared for use as shown in FIG. 4. An operator opens movable holding members 123 of injection head 110 and puts liquid syringe 200 in concave portion 114 to insert cylinder flange 213 into movable holding members 123. Then, the operator closes movable holding members 123.

When liquid syringe 200 is appropriately mounted such that flat portions 215 of cylinder flange 213 are located at the top and bottom as shown in FIG. 1B, RFID tag 230 is located on the left or right of liquid syringe 200. Then, as shown in FIG. 10B, RFID tag 230 faces reader antenna 132 (132R or 132L) in parallel to provide satisfactory magnetic coupling. This allows favorable wireless communication between RFID tag 230 and RFID reader 130.

If liquid syringe 200 is inappropriately mounted such that flat portions 215 of cylinder flange 213 are located on the left and right as shown in FIG. 1A, RFID tag 230 is located at the top or bottom of liquid syringe 200. Then, as shown in FIG. 10A, RFID tag 230 does not face reader antenna 132 (132R or 132L) in parallel and thus satisfactory magnetic coupling is not realized. As a result, RFID tag 230 cannot wirelessly communicate with RFID reader 130.

In this manner, in chemical liquid injection system 1000 of the embodiment, RFID tag 230 wirelessly communicates with RFID reader 130 when liquid syringe 200 is appropriately mounted on chemical liquid injector 100 such that flat portions 215 of cylinder flange 213 are located at the top and bottom as shown in FIG. 1B, but RFID tag 230 does not wirelessly communicate with RFID reader 130 when liquid syringe 200 is inappropriately mounted on chemical liquid injector 100 such that flat portions 215 of cylinder flange 213 are located on the left and right as shown in FIG. 1A.

Figure 12:
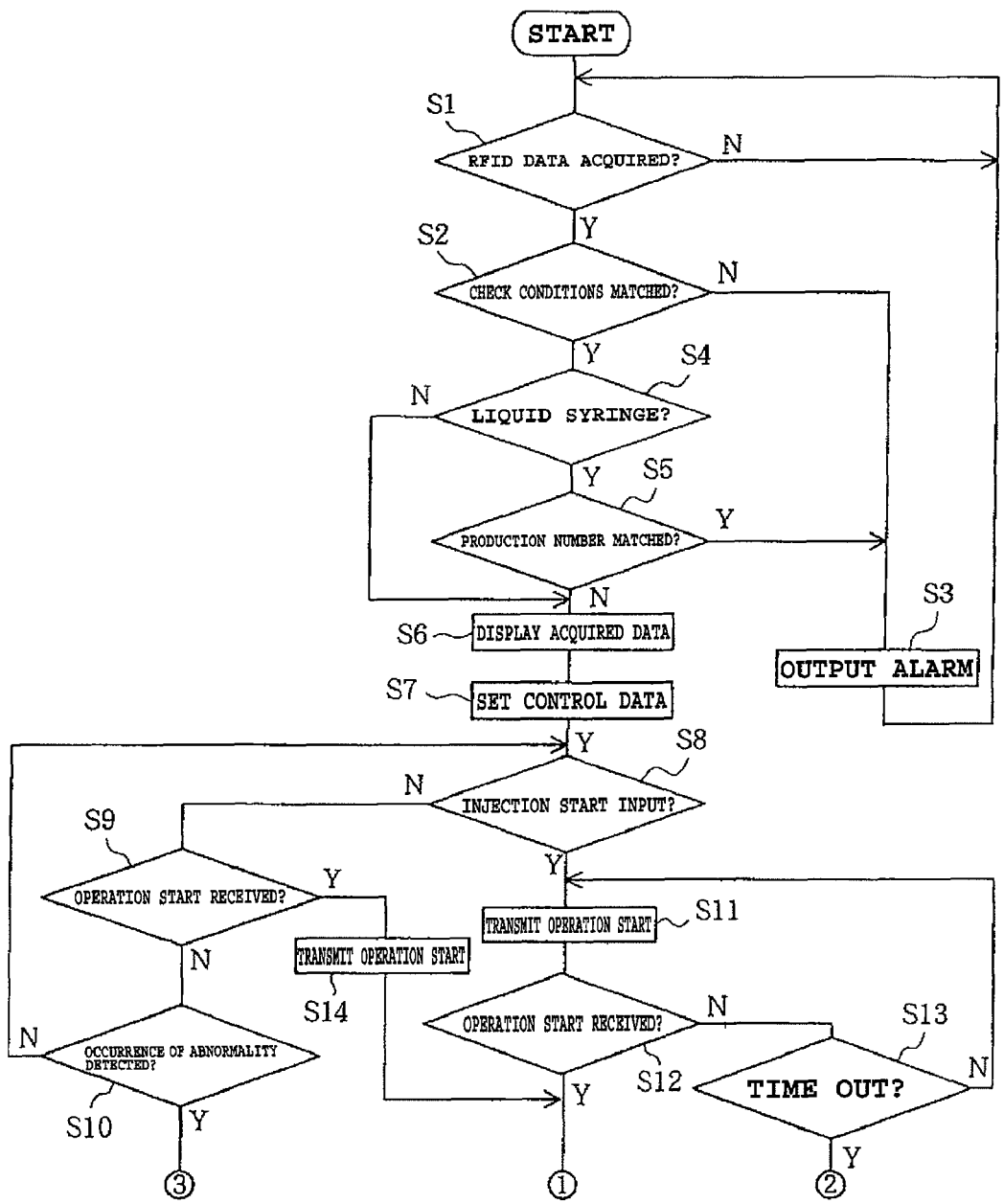
FIG. 12 is a flow chart showing the first half of processing operation in the chemical liquid injector.

Referring to FIG. 12, in chemical liquid injector 100 of the embodiment, when liquid syringe 200 is appropriately mounted on injection head 110 to cause RFID reader 130 to receive recorded data from RFID tag 230 (step S1), computer unit 140 compares the received data with the check conditions registered in RAM 143 (step S2).

The identification data of usable liquid syringes 200 is registered as such check condition. If the identification data received from RFID tag 230 is not included in the registered check conditions, a guidance message, for example "This product not registered as usable device. Check if is usable" is output as an alarm with display on liquid crystal display 104 and with sound from speaker unit 105 (step S3).

When the identification data of liquid syringe 200 matches the check conditions (step S2), the production number received from RFID tag 230 is compared with the production number registered in RAM 143 (step S5). If the compared production numbers match, a guidance message, for example "This syringe used previously. Use new one" is output as an alarm with display on liquid crystal display 104 and with sound from speaker unit 105 (step S3).

The recorded data received from RFID tag 230 of appropriate liquid syringe 200 is output with display on liquid crystal display 104, for example as "Contrast medium syringe (name) made by (manufacturer) mounted. Production number XXX, name of liquid XXX, type of liquid XXX, capacity XXX, resistance to pressure XXX" (step S6).

RFID tag 230 has data to be displayed and data not to be displayed. For example, a binary flag is set in each data to indicate whether or not the data should be displayed. Chemical liquid injector 100 appropriately selects some of the recorded data received from RFID tag 230 for display.

When the recorded data received from RFID tag 230 into chemical liquid injector 100 include control data such as "resistance to pressure," "capacity," and "variable pattern for changing the injection rate of the contrast medium over time," then the control data is set in RAM 143 of computer unit 140 (step S7). When such control data is not included in the recorded data received from RFID chip 230, default control data is set.

Liquid syringe 200 mounted on chemical liquid injector 100 is connected to a patient through an extension tube (not shown) or the like and then the operator makes entry to start operation to operation panel 103. Chemical liquid injector 100 detects the entry (step S8) and transmits a signal for starting operation to CT scanner 300 (step S11).

Figure 14:
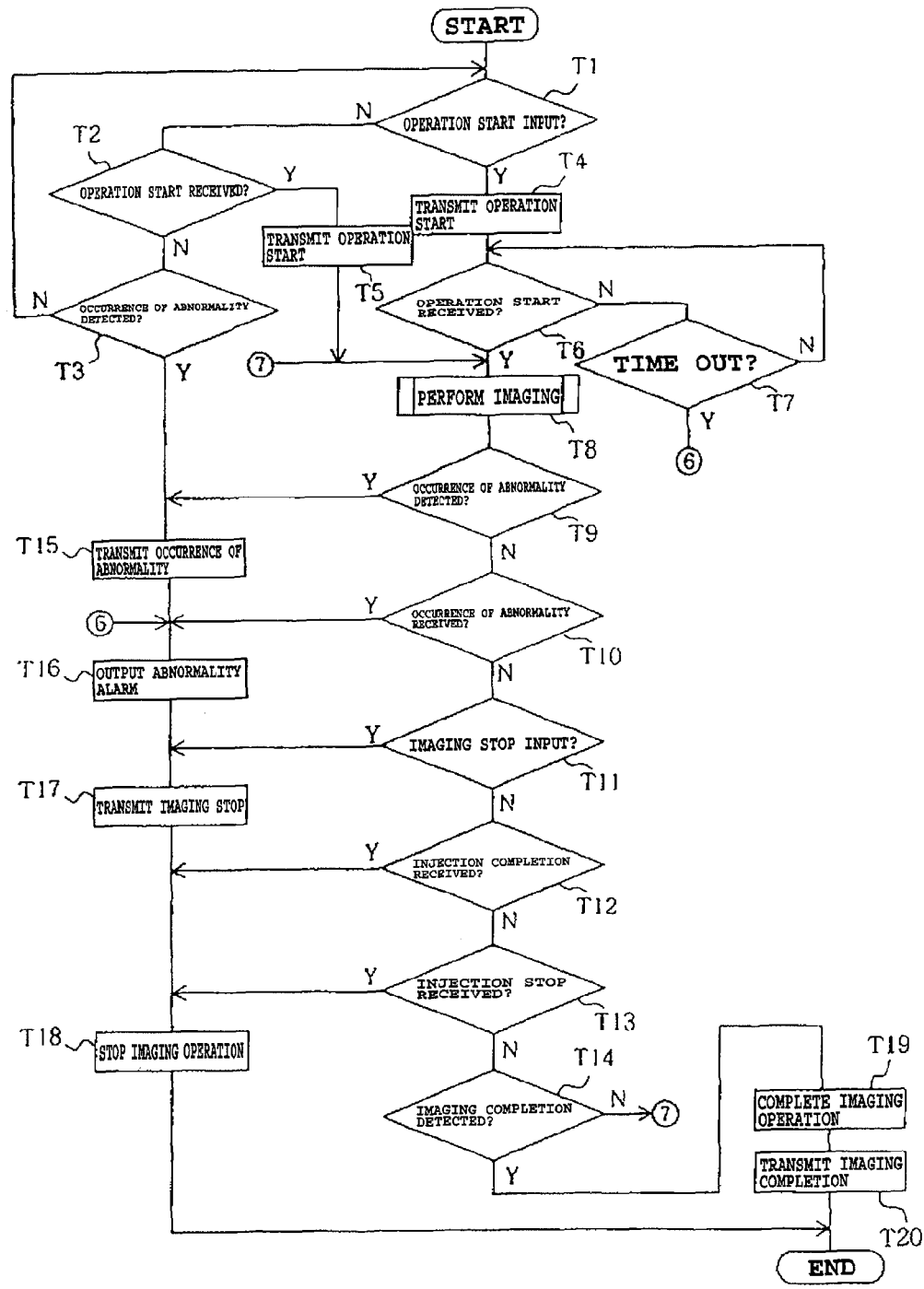
FIG. 14 is a flow chart showing processing operation in the CT scanner.

Referring to FIG. 14, CT scanner 300 receives the signal for staring operation from chemical liquid injector 100 (step T2) and transmits a signal for starting operation back to chemical liquid injector 100 (step T5) and performs imaging operation (step T8). Thus, in chemical liquid injection system 1000 of the embodiment, the imaging of CT scanner 300 follows the liquid injection of chemical liquid injector 100.

As shown in FIGS. 12 and 14, in chemical liquid injection system 1000 of the embodiment, when chemical liquid injector 100 is ready as described above (steps S8 to S10) and the operator makes entry to start operation to CT scanner 300 (step T1), the liquid injection of chemical liquid injector 100 follows the imaging of CT scanner 300 (steps T4, T6 and subsequent steps, steps S9, S18 and subsequent steps).

Figure 13:
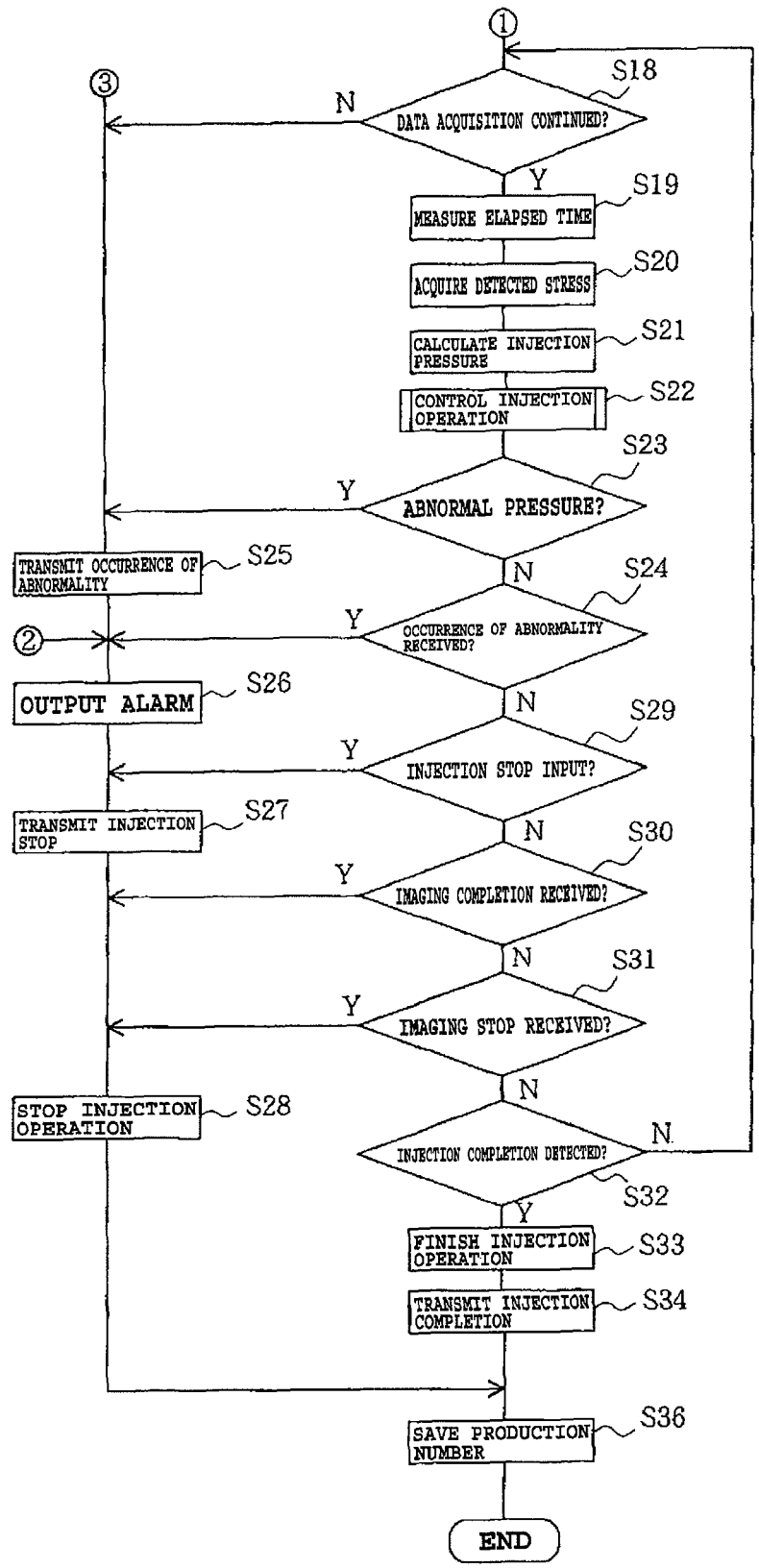
FIG. 13 is a flow chart showing the latter half.

Referring to FIG. 13, when a series of liquid injection operations is performed (step S18 and subsequent steps) in chemical liquid injector 100 of the embodiment, the elapsed time from the start of the injection is measured (step S19), and the operation of piston driving mechanism 116 is controlled in real time based on the elapsed time and the control data received from RFID tag 230 (step S22).

When the variable pattern for changing the injection rate of the contrast medium over time is recorded in RFID tag 230, the operation rate of piston driving mechanism 116 is changed over time in accordance with the variable pattern. When piston driving mechanism 116 is driven as described above, the stress detected by load cell 118 is received in real time by computer unit 140 (step S20).

The injection pressure of the liquid is calculated from the stress detected by load cell 118 (step S21) based on the viscosity of the liquid, the inner diameter of cylinder member 210 and the like received from RFID tag 230. The operation of piston driving mechanism 116 is controlled in real time such that the calculated injection pressure falls within the pressure range received from RFID tag 230 (step S23). If the resistance to pressure is recorded on RFID tag 230, the operation of piston driving mechanism 116 is controlled in accordance with the resistance to pressure.

While liquid syringe 200 is driven by piston driving mechanism 116 as described above, RFID tag 230 on liquid syringe 200 is continuously detected by RFID reader 130 (step S18). If the abovementioned detection is discontinued (step S18) before the completion of the injection operation (step S32), the injection operation performed by piston driving mechanism 116 is stopped (step S28).

In addition, a guidance message, for example "Syringe removal detected. Make sure syringe put appropriately" is output as an alarm with display on liquid crystal display 104 and with sound from speaker unit 105 (step S26). The occurrence of abnormality and the stop of injection are transmitted as a signal to CT scanner 300 (steps S25 and S28).

CT scanner 300 receives the signal representing the occurrence of abnormality (step T10) and outputs the occurrence of abnormality as an alarm with guidance display or the like (step T16). When CT scanner 300 receives the signal representing the stop of operation (step T13), the imaging operation is stopped (step T18).

In chemical liquid injector 100 and CT scanner 300 of the embodiment, when the occurrence of abnormality is detected in the abovementioned ready state (steps S10 and T3) or when the occurrence of abnormality is detected during the operation (steps S23 and T9), the occurrence of abnormality is output and notified (steps S26 and T16) and the operation is stopped (steps S28 and T18).

Since the occurrence of abnormality in one of them is transmitted to the other (steps S25 and T15), the other receives the data (steps T10 and S24) and then outputs and notifies the occurrence of abnormality (steps T16 and S26). Since the operation stop in one of them is transmitted to the other (steps S27 and T17), the other receives the data (steps T13 and S31) and stops the operation (steps T18 and S28).

When one of chemical liquid injector 100 and CT scanner 300 receives entry to stop operation (steps S29 and T11), the one stops the operation (steps S28 and T18) and transmits it to the other (steps S27 and T17). The other receives the data (steps T13 and S31) and stops the operation (steps T18 and S28).

When the completion of the operation is detected in one of chemical liquid injector 100 and CT scanner 300 (steps S32 and T14), the operation is ended (steps S33 and T19) and the end of the operation is transmitted to the other (steps S34 and T20). The other receives the data (steps T12 and S31) and stops the operation (steps T18 and S28).

In chemical liquid injector 100 of the embodiment, when the injection operation is finished normally or abnormally as described above (step S33 or S28), the identification data received from RFID tag 230 on liquid syringe 200 is registered as the check condition in RAM 143 (step S36).

Effect of the Embodiment

In chemical liquid injection system 1000 of the embodiment, RFID tag 230 having the various types of data recorded thereon is placed on liquid syringe 200 as described above. Chemical liquid injector 100 receives the data from RFID tag 230 and performs the predetermined operation in accordance with at least some of the received data. In this manner, a large amount of data can be easily entered into chemical liquid injector 100 to perform various operations.

In chemical liquid injection system 1000 of the embodiment, only when liquid syringe 200 is appropriately held by cylinder holding mechanism 120, RFID tag 230 wirelessly communicates with RFID reader 130. Only when RFID tag 230 wirelessly communicates with RFID reader 130 in this manner, the operation of piston driving mechanism 116 is permitted. This can automatically prevent piston member 220 from being pressed into cylinder member 210 while liquid syringe 200 is not appropriately held.

In chemical liquid injector 100 of the embodiment, computer unit 140 allows piston driving mechanism 116 to operate only when RFID reader 130 detects RFID tag 230. If liquid syringe 200 is displaced from the appropriate position during the liquid injection, the liquid injection operation can be stopped automatically.

Since the mechanism for detecting the appropriate mounting of liquid syringe 200 is formed of RFID tag/reader 230 and 130 for transmitting the data from liquid syringe 200 to chemical liquid injector 100, the appropriate mounting of liquid syringe 200 can be detected by using the simple structure without requiring a dedicated sensor mechanism or the like.

The wireless communication between RFID tag 230 and RFID reader 130 is generally prevented by liquid. In the embodiment, however, reader antennas 132L and 132R are placed on the left and right of the position at which liquid syringe 200 is mounted as shown in FIG. 1B, so that favorable wireless communication can be performed whether RFID tag 230 is placed on the left or right as long as liquid syringe 200 is appropriately mounted.

In addition, in chemical liquid injector 100 of the embodiment, reader antennas 132L and 132R on the left and right produce central magnetic fields B in the same direction on the left and right as shown in FIG. 10B. This can enhance the magnetic fields of reader antennas 132L and 132R on the left and right continuously and mutually to improve the communication sensitivity of RFID reader 130.

Reader antennas 132L and 132R on the left and right are formed of the single wire and are connected to single reader circuit 131. This eliminates the need to form or drive reader antennas 132L and 132R on the left and right individually to enable the simple structure and enables reliable synchronization between the communication operations of reader antennas 132L and 132R.

Since it is contemplated that chemical liquid injector 100 of the embodiment is manufactured by partially changing an existing product, head body 113 on which cylinder body 211 of liquid syringe 200 is mounted is made of metal such as an alloy of aluminum. The communication performance of RFID reader 130 achieved through electromagnetic induction is impaired if metal is present near reader antenna 132.

In chemical liquid injector 100 of the embodiment, however, as shown in FIGS. 8 and 9, reader antenna 132 is mounted at the position away from the outer edge of the front side of insulating substrate 135 which is placed in through hole 119 of head body 113. Thus, the inner edge of through hole 119 of head body 113 is spaced from the outer edge of reader antenna 132 by the predetermined spatial distance. With this structure, reader antenna 132 can perform wireless communication through electromagnetic induction without being impaired by head body 113 made of metal.

Chemical liquid injector 100 based on the existing product as described above includes injection head 110 and injection control unit 101 formed as the separate components, and injection head 110 placed near a patient is extremely reduced in size. For this reason, it is difficult to mount reader circuit 131 on injection head 110, and thus reader circuit 131 is mounted on injection control unit 101.

This configuration lengthens the wiring connecting reader circuit 131 to reader antenna 132, which makes it difficult for reader circuit 131 to detect a very weak signal from reader antenna 132 favorably. To address this, in chemical liquid injector 100 of the embodiment, reader circuit 131 and reader antenna 132 are connected to each other through the coaxial cable with equal impedance. It is thus possible for reader circuit 131 to detect a very weak signal from reader antenna 132 and it is unnecessary to increase the size of injection head 110 for mounting reader circuit 131 thereon.

Since it is also assumed that RFID tag 230 of the embodiment is realized by an existing product, RFID tag 230 is formed in the predetermined elongated shape. If tag antenna 233 which is the loop antenna in such an elongated shape is bent along its longitudinal direction, the communication performance thereof is extremely reduced. In liquid syringe 200 of the embodiment, the longitudinal direction of cylinder member 210 coincides with the longitudinal direction of RFID tag 230. Tag antenna 233 is slightly curved in a direction orthogonal to the longitudinal direction but is not bent along the longitudinal direction, thereby realizing favorable communication performance.

The communication performance of RFID tag 230 is also inhibited by liquid. RFID tag 230 needs to be mounted with its longitudinal direction coincident with the longitudinal direction of cylinder member 210 as described above, so that it is difficult to place RFID tag 230 at a position on cylinder member 210 where no liquid is present.

In liquid syringe 200 of the embodiment, however, cylinder member 210 is formed to have a sufficient thickness of 1.5 mm to 2.0 mm. This allows RFID tag 230 attached to the surface thereof to perform excellent wireless communication without being inhibited by the liquid contained in cylinder member 210.

In chemical liquid injector 100 of the embodiment, reader antenna 132 is also formed in the elongated shape. When liquid syringe 200 is put in concave portion 114, the longitudinal direction of tag antenna 233 coincides with the longitudinal direction of reader antenna 132. This enables favorable wireless communication between RFID tag 230 and RFID reader 130. Reader antenna 132 has the plurality of circular loop antennas 133 arranged in parallel, which can realize reader antenna 132 of the elongated shape functioning effectively with the simple structure.

In chemical liquid injection system 1000 of the embodiment, at least some of the data received from RFID tag 230 are held and output with display on liquid crystal display 104, so that an operator can check the data of liquid syringe 200 to be used and the like easily and reliably.

Chemical liquid injector 100 of the embodiment compares the check conditions stored as data with the data received from RFID tag 230, and as required, outputs the alarm. For example, when the operator attempts to use liquid syringe 200 which is not allowed in chemical liquid injector 100 or liquid syringe 200 with the expiration date elapsed, the alarm can be output to prevent any medical malpractice reliably.

Particularly, in chemical liquid injector 100 of the embodiment, when the data is read from RFID tag 230, the production number for each liquid syringe 200 is stored. If the production number newly received from RFID tag 230 is already stored, the alarm is output. It is thus possible to readily and reliably prevent medical malpractice such as repeated use of liquid syringe 200 which should be discarded after it is used once.

In chemical liquid injection system 1000 of the embodiment, when the variable pattern for changing the injection rate of the constant medium over time is recorded on RFID tag 230 on liquid syringe 200 of the pre-filled type filled with the contrast medium, chemical liquid injector 100 changes the injection rate of the contrast medium over time in accordance with the variable pattern.

Consequently, the optimal image contrast can be maintained favorably, and the minimum amount of the injected contrast medium can be used to reduce physical burdens on the patient. In addition, it is not necessary to previously register the data of the complicated variable pattern in chemical liquid injector 100. For example, a new variable pattern for a new contrast medium can be simply input as data into chemical liquid injector 100 from RFID tag 230 on liquid syringe 200.

In chemical liquid injector 100 of the embodiment, the pressure of the injected liquid is detected from the stress applied to piston member 220 of liquid syringe 200, and if the injection pressure reaches an abnormal value, the alarm is output and the injection operation is forcedly stopped. This can prevent medical malpractice of injection of the liquid at an abnormal pressure.

The accurate detection of the pressure of the liquid by chemical liquid injector 100 as described above requires not only the stress applied to piston member 220 of liquid syringe 200 but also the data such as the inner diameter of cylinder member 210 and the viscosity of the liquid. The data is input into chemical liquid injector 100 from RFID tag 230. This eliminates the need for the operator to perform complicated operations of manual entry of the various types of data into chemical liquid injector 100 and chemical liquid injector 100 can appropriately detect the injection pressure of each liquid for each liquid syringe 200 in chemical liquid injection system 1000 of the embodiment.

In chemical liquid injection system 1000 of the embodiment, since the liquid injection in chemical liquid injector 100 is automatically associated with the imaging in CT scanner 300, the diagnostic images can be taken in an appropriate timing from the patient injected with the contrast medium in an appropriate timing.

Modifications of the Embodiment

The present invention is not in any way limited to the abovementioned embodiment, but various changes and modifications may be made therein without departing from the scope of the invention. For example, in the above embodiment, circular loop antennas 133 are placed in parallel in order to form reader antenna 132 in the elongated shape. Alternatively, a single oval loop antenna may be used or three or more circular loop antennas may be arranged in parallel (neither shown).

In the above embodiment, reader antenna 132 is formed of the wire on one side of insulating substrate 135, but the reader antenna may be formed of printed wiring or formed on the back side of the insulating substrate as shown in FIGS. 15A, 15B, 16A, and 16B, for example.

Figure 15A:
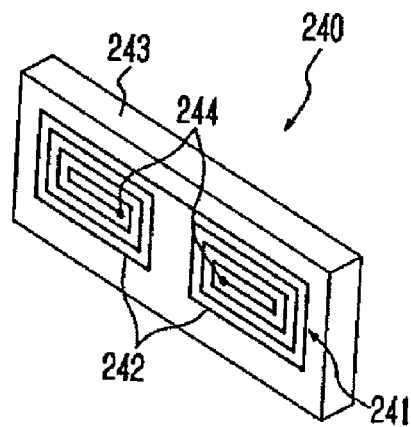
FIG. 15A is a perspective view showing a first modification of the reader antenna.
Figure 15B:
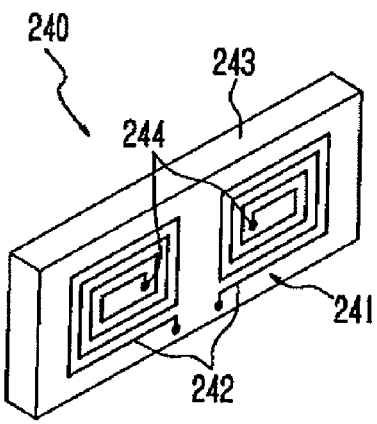
FIG. 15B is a perspective view showing the first modification of the reader antenna.

More particularly, antenna unit 240 illustrated in FIGS. 15A and 15B includes reader antenna 241 formed of printed wiring on the front and back sides of insulating substrate 243. Reader antenna 241 has two rectangular loop antennas 242 arranged in parallel on the front of rectangular insulating substrate 243 and two rectangular loop antennas 242 arranged in parallel on the back of insulating substrate 242. In antenna unit 240, since loop antennas 242 on the front and back of insulating substrate 243 are connected to each other with through hole 244, the front and back of insulating substrate 243 are effectively used to provide reader antenna 241.

Figure 16A:
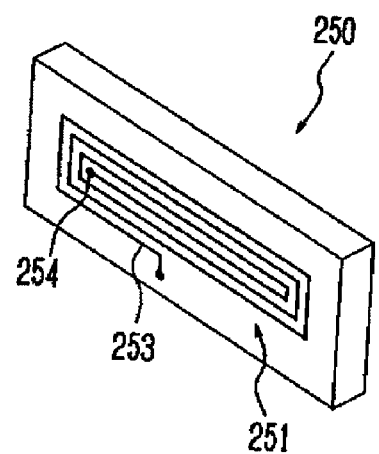
FIG. 16A is a perspective view showing a second modification of the reader antenna.
Figure 16B:
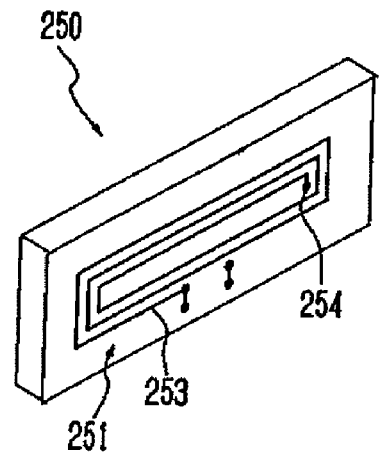
FIG. 16B is a perspective view showing the second modification of the reader antenna.

Antenna unit 250 shown in FIGS. 16A and 16B includes reader antenna 251 formed on the front and back of an insulating substrate. Reader antenna 251 has one rectangular loop antenna 253 formed on the front side of the rectangular insulating substrate and one rectangular loop antenna 253 on the back side thereof. In antenna unit 250, since loop antennas 253 on the front and back of insulating substrate 252 are connected to each other with through hole 254, both sides of insulating substrate 252 are effectively used to provide reader antenna 251.

In the above embodiment, to match the directions of central magnetic fields B of paired reader antennas 132L and 132R on the left and right, all of loop antennas 133 are wound in the same direction, forward loop antenna 133 on the left is connected to rearward loop antenna 133 on the right, and rearward loop antenna 133 on the left is connected to forward loop antenna 133 on the right as shown in FIGS. 10A and 10B.

Figure 17:
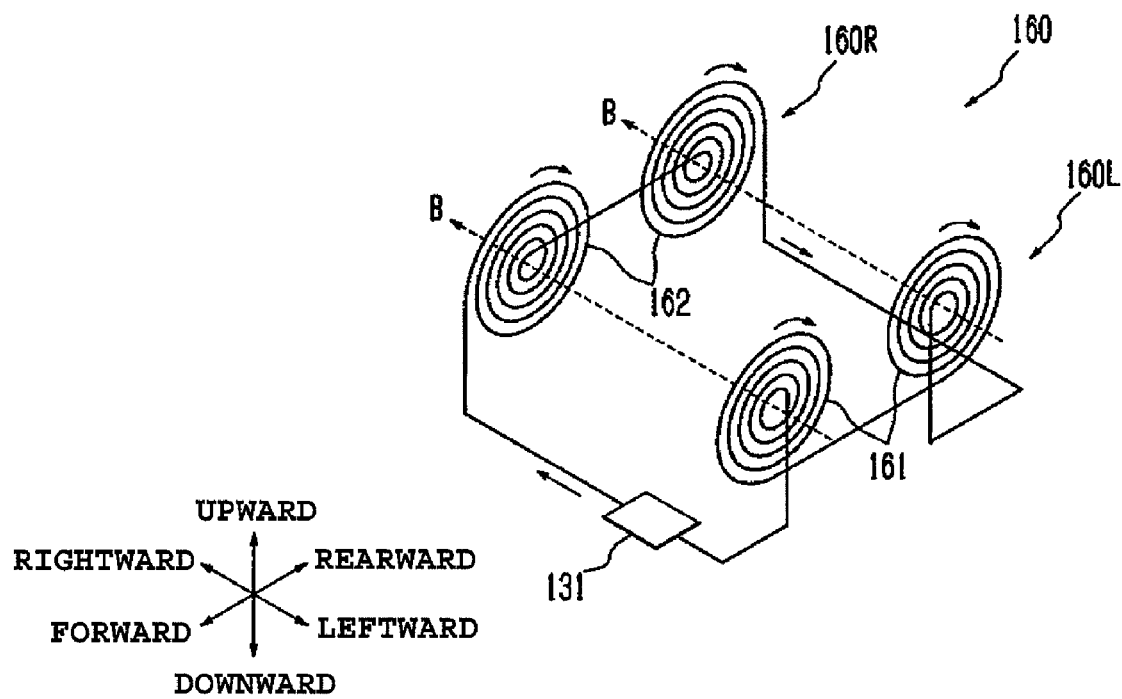
FIG. 17 is a perspective view showing a third modification of the reader antenna.

Alternatively, as in reader antenna 160 show in FIG. 17, it is possible that loop antennas 161 and 162 on the left and right are wound in reverse directions, forward loop antenna 161 on the left is connected to forward loop antenna 162 on the right, and rearward loop antenna 161 on the left is connected to rearward loop antenna 162 on the right.

In the above embodiment, the entire cylinder member 210 is formed to have the thickness determined such that the liquid contained in cylinder member 210 does not prevent electromagnetic induction with RFID tag 230. For example, if the cylinder member does not have a sufficient thickness, it can be formed to have a predetermined thickness only in its portion where RFID tag 230 is put, or RFID tag 230 can be put over the cylinder member with a base made of resin interposed between them (neither shown).

It is also possible that a magnetic material 260 such as ferrite is formed into a sheet shape similar to RFID tag 230, and RFID tag 230 is placed over the outer circumference of cylinder member 210 with the magnetic material interposed between them (FIGS. 1A and 1B). In this case, since the magnetic field on the back of RFID tag 230 passes through the magnetic material 260 the magnetic field can be prevented from being absorbed by the liquid contained in cylinder member 210, thereby improving the communication performance of RFID tag 230.

It is also possible that a magnetic material 160 is formed into a sheet shape similar to the reader antenna and is placed on the back of reader antenna 132 to allow the magnetic field on the back of reader antenna 132 to pass through the magnetic material 160 (FIGS. 1A and 1B). This enables improved communication performance of RFID reader 130.

In the above embodiment, reader antenna 132 is disposed in through hole 119 of head body 113 in order for head body 113 made of metal not to prevent wireless communication of reader antenna 132. For example, if the head body is made of nonmagnetic material such as resin, reader antenna 132 may be placed directly on the surface of the head body or the like without forming any through hole.

Since a large stress is applied to cylinder flange 213 of liquid syringe 200 from which the chemical liquid is injected at high pressure, flange holding member 121 for holding cylinder flange 213 is desirably made of metal. Thus, if the head body is made of nonmagnetic material such as resin as described above, reader antenna 132 is preferably placed at a position away from flange holding member 121 made of metal by a predetermined spatial distance.

In the above embodiment, reader antenna 132 on injection head 110 is connected to reader circuit 131 on injection control unit 101 through the coaxial cable to favorably transmit the very weak signal of RFID tag 230 from reader antenna 132 to reader circuit 131. Alternatively, the reader circuit may also be mounted on the injection head to transmit the very weak signal of RFID tag 230 more favorably from the reader antenna to the reader circuit (not shown).

Figure 18A:
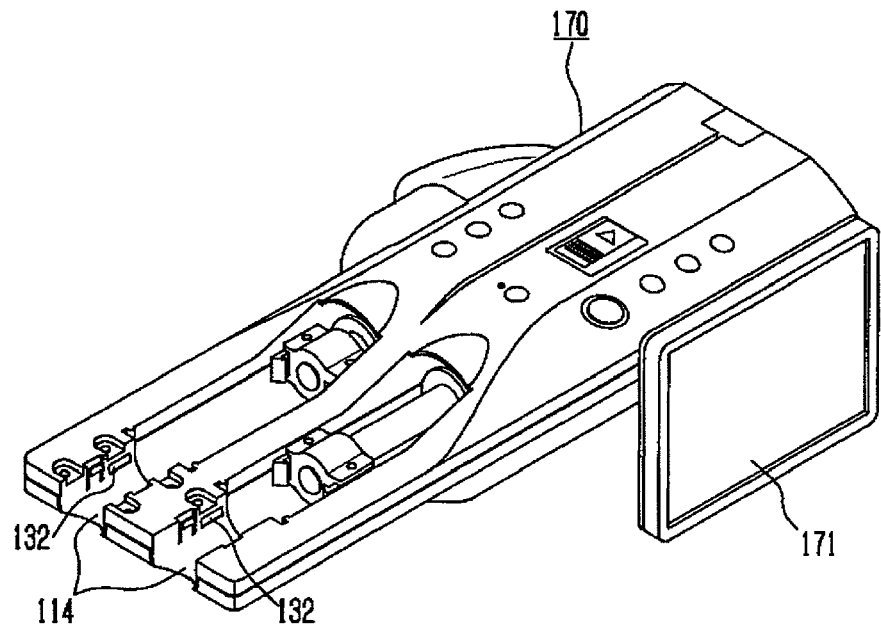
FIG. 18A is a perspective view showing a modification of the injection head.
Figure 18B:
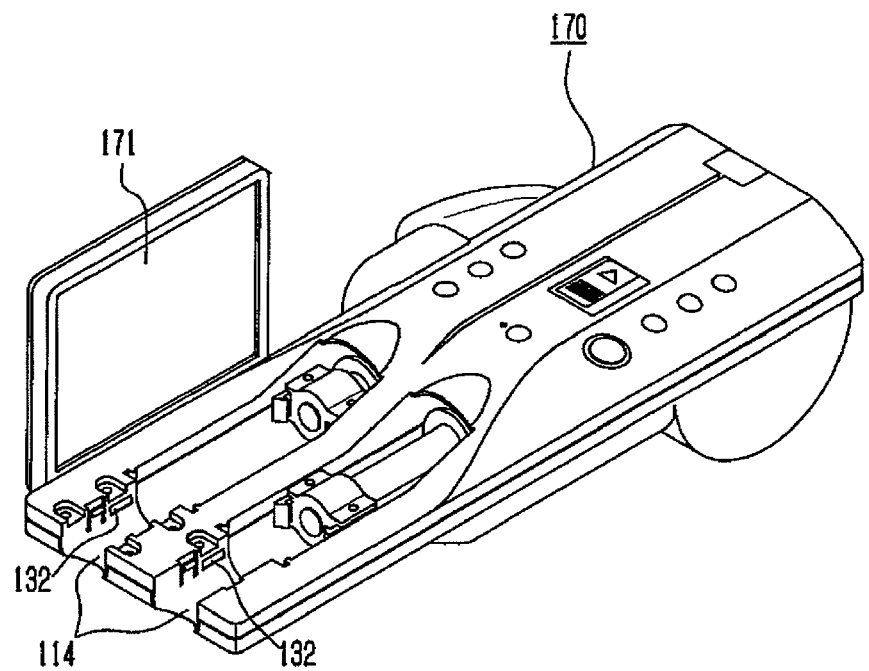
FIG. 18B is a perspective view showing a modification of the injection head.

The above embodiment has shown chemical liquid injector 100 in which injection head 110 has one concave portion 114 for mounting only one liquid syringe 200 therein. As shown in FIGS. 18A and 18B, a plurality of concave portions 114 may be provided for injection head 170 to realize a chemical liquid injector (not shown) on which a plurality of liquid syringes 200 are mounted.

In this case, RFID antenna 132 may be placed for each of concave portions 114 of injection head 170 to detect recorded data from each of RFID tags 230 on liquid syringes 200. Since RFID reader 130 can detect data on a plurality of RFID tags 230 in a time-division manner, RFID reader 130 may include one RFID circuit 131 and a plurality of reader antennas 132 placed in a plurality of concave portions 114.

In the above embodiment, the recorded data detected by RFID reader 130 from RFID tag 230 is output with display on liquid crystal display 104 of injection control unit 101 formed as the separate component from injection head 110. However, as shown in FIGS. 18A and 18B, injection head 170 may be provided with display panel 171 on which data recorded on RFID tag 230 may be displayed.

In this case, immediately after liquid syringe 200 is appropriately mounted in injection head 170, recorded data is output on display panel 171. This allows immediate check of appropriate mounting of liquid syringe 200 and intuitive recognition of the displayed data.

Figure 19:
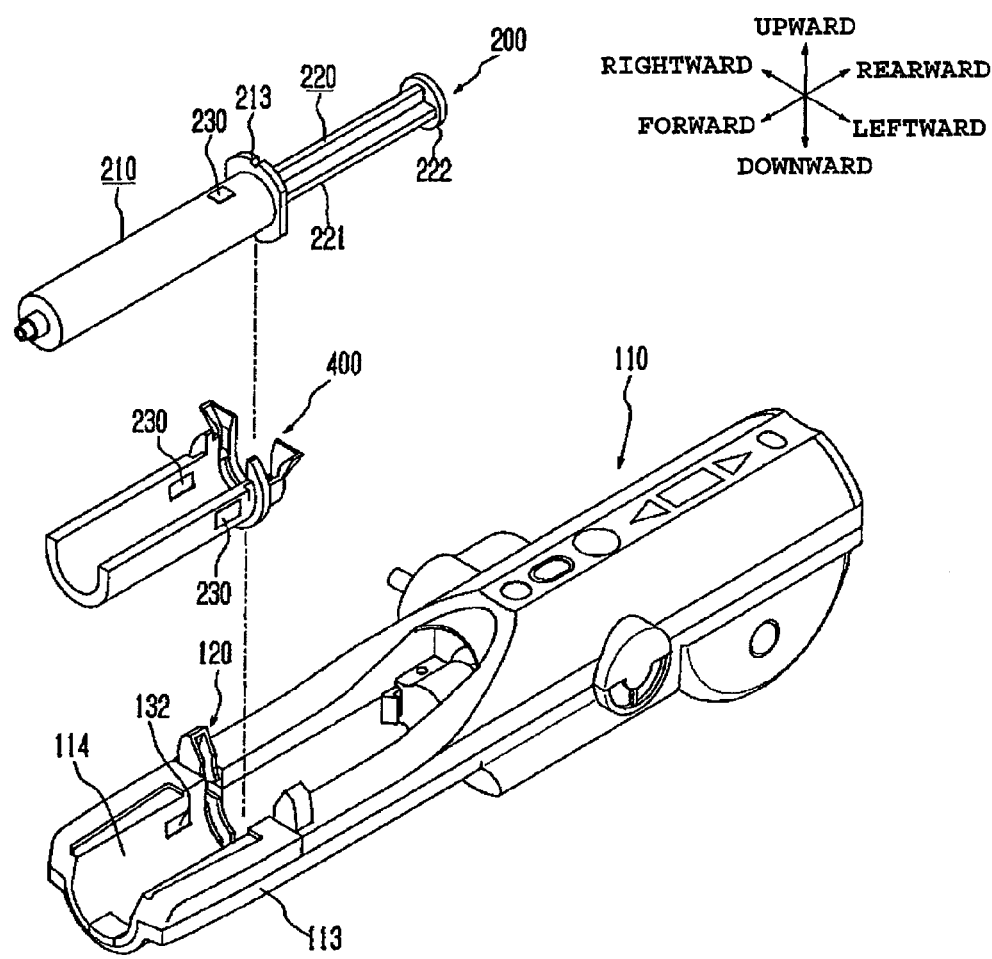
FIG. 19 is a perspective view showing a modification of the chemical liquid injection system in which a liquid syringe is mounted over an injection head with a cylinder adapter interposed between them.

In the above embodiment, liquid syringe 200 of one size is mounted on chemical liquid injector 100 to simplify the description. In a chemical liquid injection system actually implemented by the present inventor, however, liquid syringes 200 of a plurality of sizes differing particularly in diameter are used. As shown in FIG. 19, cylinder adapter 400 is provided for each size of liquid syringe 200 other than the maximum diameter.

In such a chemical liquid injection system, liquid syringe 200 having the maximum diameter is directly mounted on chemical liquid injector 100, and liquid syringe 200 of a size other than the maximum diameter is mounted with cylinder adapter 400 used between them. RFID tag 230 may be put on the outer circumference and inner circumference of cylinder adapter 400 opposite to reader antenna 132 in parallel when cylinder adapter 400 is appropriately mounted on chemical liquid injector 100.

In this case, chemical liquid injector 100 can check appropriate mounting of both of cylinder adapter 400 and liquid syringe 200, and can compare recorded data of cylinder adapter 400 with recorded data of liquid syringe 200 to see whether or not the combination of liquid syringe 200 and cylinder adapter 400 is proper.

Since RFID reader 130 can wirelessly communicate with a plurality of RFID tags 230 as described above, one RFID reader 130 can wirelessly communicate with RFID tags 230 of both of cylinder adapter 400 and liquid syringe 200 in chemical liquid injector 100.

Since RFID tag 230 on liquid syringe 200 faces reader antenna 132 on chemical liquid injector 100 with cylinder adapter 400 interposed between them in the abovementioned chemical liquid injection system, cylinder adapter 400 is preferably formed of nonmagnetic material such as resin which does not prevent wireless communication between RFID tag 230 and RFID reader 130.

In the above embodiment, to use liquid syringe 200 and the like only once, the production number of each liquid syringe 200 is received by RFID reader 130 from RFID tag 230 of liquid syringe 200 to be used, and is stored in chemical liquid injector 100. If a newly received connection number is already stored, the alarm is output.

Alternatively, it is possible that a rewritable product is used as RFID tag 230, chemical liquid injector 100 records, on RFID tag 230 of liquid syringe 200, the "used" or the fact that liquid syringe 200 has been mounted and the liquid therein has been injected, and an alarm is output when the data "used" is received from RFID tag 230 of newly mounted liquid syringe 200.

Since a large number of production numbers do not need to be stored in chemical liquid injector 100 in this case, an overflow or the like of RAM 143 can be prevented, and RAM 143 having a large capacity does not need to be included uselessly. In addition, even when the data stored in chemical liquid injector 100 is reset erroneously, inappropriately repeated use of liquid syringe 200 or the like can be prevented.

In the above embodiment, the control data for the liquid injection is received from RFID tag 230 and the like into chemical liquid injector 100, and chemical liquid injector 100 controls the operation of the liquid injection based on the control data. It is also possible that chemical liquid injector 100 controls the operation of the liquid injection based on a combination of control data received from RFID tag 230 on liquid syringe 200 and control data entered through operation panel 103 or the like.

For example, it is possible that the variable pattern of liquid injection over time is recorded on RFID tag 230 on liquid syringe 200 as described above, and when an operator enters the data of an area to be imaged by CT scanner 300 through operation panel 103 or the like, the variable pattern is adjusted in accordance with the area to be imaged.

In the above embodiment, chemical liquid injector 100 finishes the injection and registers the production number received from RFID tag 230 on liquid syringe 200, and then ends the operation. Alternatively, for example, it is possible that when chemical liquid injector 100 finishes the injection and registration of the production number as described above and detects removal of liquid syringe 200 with RFID reader 130, chemical liquid injector 100 automatically moves piston driving mechanism 116 backward to the initial position at the backend.

It is also possible that when chemical liquid injector 100 completes the operation and moves piston driving mechanism 116 back to the initial position and then detects the mounting of new liquid syringe 200 with RFID reader 130, chemical liquid injector 100 automatically moves piston driving mechanism 116 forward to the standby position for holding piston members 210. In this case, liquid syringe 200 can be removed and put in chemical liquid injector 100 in an appropriate timing to place piston driving mechanism 116 automatically to the appropriate position, so that any special operation is unnecessary to place piston driving mechanism 116 and the convenience can be improved.

In the above embodiment, the various types of data are recorded on RFID tag 230 by the manufacturer. Alternatively, the various types of data may be recorded on RFID tag 230 or the like in a medical facility such as a hospital where liquid syringe 200 is used.

In this case, desired data can be provided for liquid syringe 200 in the medial facility, and for example when a desired liquid is filled into liquid syringe 200 of the type filled with nothing, data of that liquid can be recorded on RFID tag 230. In such a case, however, it is preferable that the production number is previously recorded inflexibly on RFID tag 230 to prevent repeated use of liquid syringe 200 as described above.

In the above embodiment, CT scanner 300 is used as the imaging diagnostic apparatus and chemical liquid injector 100 injects the contrast medium for CT. For example, an MRI apparatus or a PET apparatus may be used as the imaging diagnostic apparatus and the chemical liquid injector may inject a contrast medium therefor.

In the above embodiment, the respective portions of chemical liquid injector 100 have been specifically described, but the portions may be changed in various manners. For example, the driving source of the piston driving mechanism may be realized by a DC (Direct Current) motor or an AC (Alternating Current) motor, or the display panel may be realized by an organic EL (Electro-Luminescence) display or a plasma display (not shown).

In the above embodiment, CPU 141 operates in accordance with the computer program stored in RAM 143 or the like to realize logically various means as the functions of chemical liquid injector 100. Each of the various means may be formed as specific hardware, or some of them may be stored as software in ROM 143 or the like, while others may be formed as hardware.

The invention claimed is:

1. A chemical liquid injection system comprising:
   a liquid syringe having a piston member slidably inserted into a cylinder member having a tubular shape, the cylinder member has a cylinder flange formed on a trailing end of a cylinder body, and the cylinder flange has a pair of flat portions in parallel at opposite positions on its outer circumference; and
   a chemical liquid injector for injecting a liquid into a patient by pressing the piston member into the cylinder member of the liquid syringe mounted interchangeably thereon,
   wherein an RFID tag including a tag antenna formed of a loop antenna is positioned on an outer circumference of the cylinder member, and
   the chemical liquid injector includes a cylinder holding mechanism for holding the cylinder member, a piston driving mechanism for pressing the piston member into the held cylinder member, an RFID reader for receiving data from the RFID tag through electromagnetic induction via a pair of reader antennas formed of loop antennas and connected to each other, a processor configured to permit operation of the piston driving mechanism only when the data is received and an antenna placement portion for placing the paired reader antennas at opposite positions across the axis of the cylinder member and one of the reader antennas at a position opposite to the tag antenna generally in parallel while the cylinder member is appropriately held by the cylinder holding mechanism such that the flat portions of the cylinder flange are located at the top and the bottom.

2. The chemical liquid injection system according to claim 1, wherein the paired reader antennas are placed such that the positions of central magnetic fields of the paired reader antennas coincide.

3. The chemical liquid injection system according to claim 1, wherein the RFID tag is located on the left or right of the cylinder member held appropriately by the cylinder holding mechanism, and
   the paired reader antennas are placed on the left and right of the cylinder member held by the cylinder holding mechanism.

4. The chemical liquid injection system according to claim 1, wherein the chemical liquid injector has a cylinder holding member made of metal having a concave portion in a semi-cylindrical shape for holding the cylinder member when the cylinder member is fitted therein,
   the cylinder holding member has a pair of through hole formed therein,
   the reader antennas are placed in the through hole, and
   outer edges of the reader antennas are spaced from inner edges of the through hole by a predetermined spatial distance.

5. The chemical liquid injection system according to claim 1, wherein
   the chemical liquid injector has a pair of flange holding members made of metal for holding the cylinder flange, and the reader antennas are placed at a position away from the flange holding members by a predetermined spatial distance.

6. The chemical liquid injection system according to claim 1, wherein at least a portion of the liquid syringe is formed to have a predetermined thickness, the tag antenna being located on that portion.

7. The chemical liquid injection system according to claim 1, wherein the tag antenna is placed over a surface of the cylinder member with a magnetic material of a sheet shape interposed between them.

8. The chemical liquid injection system according to claim 1, wherein magnetic materials of a sheet shape are placed on surfaces of the reader antennas opposite to a surface thereof facing the tag antenna in the chemical liquid injector.

9. The chemical liquid injection system according to claim 1, wherein the chemical liquid injector includes:
   an injection head including the cylinder holding mechanism, the piston driving mechanism, the paired reader antennas, and the antenna placement mechanism; and
   an injection control unit including the processor and a reader circuit connected to the reader antenna, the injection control unit being formed as a separate component from the injection head, and
   the reader antennas are connected to the reader circuit through a coaxial cable.

10. The chemical liquid injection system according to claim 1, wherein the chemical liquid injector includes:
    an injection head including the cylinder holding mechanism, the piston driving mechanism, the paired reader antennas, the antenna placement mechanism, and a reader circuit connected to the reader antenna; and
    an injection control unit including the processor, the injection control unit being formed as a separate component from the injection head.

11. The chemical liquid injection system according to claim 1, wherein the chemical liquid injector includes a display configured to display at least part of the data received from the RFID tag.

12. The chemical liquid injection system according to claim 9, wherein a display unit is mounted on the injection head and the chemical liquid injection system has data display means for displaying at least part of data received from the RFID tag.

13. The chemical liquid injection system according to claim 1, wherein the processor is configured to returns the piston driving mechanism to an initial position after the completion of liquid injection operation is detected and wherein the detection of the RFID tag by the RFID reader subsequently ends.

14. The chemical liquid injection system according to claim 1, wherein the processor includes a memory configured to hold data received from the RFID tag, and wherein the processor is configured to control operation of the piston driving mechanism based on at least some of the held data.

15. The chemical liquid injection system according to claim 14, wherein the liquid syringe is of a pre-filled type shipped after it is filled, as the liquid, with a contrast medium to be injected into a patient whose diagnostic image is taken by an imaging diagnostic apparatus, the RFID tag on the liquid syringe having data of a variable pattern recorded thereon for changing an injection rate of the contrast medium over time, and the processor is configured to change an operation rate of the piston driving mechanism over time in accordance with the variable pattern.

16. The chemical liquid injection system according to claim 1, wherein the processor includes a memory for storing predetermined check conditions, wherein the processor is configured to compare the stored check conditions with data received from the RFID tag, and wherein the processor is configured to trigger an alarm in accordance with the comparison result.

17. The chemical liquid injection system according to claim 1, wherein the liquid syringe is provided with a plurality of sizes differing in diameter, a cylinder adapter is provided for each size of the liquid syringe other than the maximum diameter, the chemical liquid injector is formed such that the liquid syringe of the maximum diameter is directly put on the cylinder holding mechanism and the liquid syringe of a size other than the maximum diameter is put over the cylinder holding mechanism with the cylinder adapter interposed between them, and the cylinder adapter is made of nonmagnetic material, and an RFID tag is put thereon at a position opposite to the reader antenna when the cylinder adapter is mounted on the cylinder holding mechanism.

18. The chemical liquid injection system according to claim 1, wherein the RFID tag on the liquid syringe has, recorded thereon, identification data associated with the size of the liquid syringe, the RFID tag on the cylinder adapter has, recorded thereon, the identification data associated with the size of the liquid syringe held on the cylinder adapter, and the operation control means includes data identifying means for comparing identification data received from the RFID tag on the liquid syringe with identification data received from the RFID tag on the cylinder adapter and alarm outputting means for outputting an alarm if the identification data do not match.

19. The chemical liquid injection system according to claim 1, wherein the RFID tag on the liquid syringe has at least a production number for each item of the liquid syringe set thereon, and the processor includes a memory configured to store the production number of the liquid syringe mounted and used to perform injection operation, and wherein the processor is configured to compare the stored production number with a newly stored production number, and trigger an alarm when the compared production numbers match.

20. The chemical liquid injection system according to claim 1, wherein the RFID tag on the liquid syringe is rewritable, and the chemical liquid injector records, on the RFID tag on the liquid syringe, data "used" representing the fact that the liquid syringe has been mounted and used to perform injection operation, and the alarm is triggered when the data "used" is received from the RFID tag on the liquid syringe.

21. The chemical liquid injector used for the chemical liquid injection system according to claim 1, comprising:

the cylinder holding mechanism for holding the cylinder member, the piston driving mechanism for injecting the liquid into the patient by pressing the piston member into the held cylinder member;

the RFID reader for receiving data from the RFID tag through electromagnetic induction via the pair of reader antennas formed of loop antennas and connected each other;

the processor is configured to permit operation of the piston driving mechanism only when the data is received; and the antenna placement portion for placing the pair of reader antennas at opposite positions across the axis of the cylinder member and one of the reader antennas at a position opposite to the tag antenna generally in parallel while the cylinder member is appropriately held by the cylinder holding mechanism such that the flat portions of the cylinder flange are located at the top and the bottom.

* * * * *